(12) United States Patent
Paul, Jr.

(10) Patent No.: US 8,506,583 B2
(45) Date of Patent: Aug. 13, 2013

(54) METHOD FOR OPEN SURGICAL PLACEMENT

(75) Inventor: Ram H. Paul, Jr., Bloomington, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 0 days.

(21) Appl. No.: 13/593,088

(22) Filed: Aug. 23, 2012

(65) Prior Publication Data
US 2012/0330331 A1    Dec. 27, 2012

Related U.S. Application Data

(62) Division of application No. 12/257,063, filed on Oct. 23, 2008, now abandoned.

(60) Provisional application No. 60/982,868, filed on Oct. 26, 2007, provisional application No. 61/127,308, filed on May 12, 2008.

(51) Int. Cl.
*A61B 17/22* (2006.01)

(52) U.S. Cl.
USPC .......................................... 606/155

(58) Field of Classification Search
USPC ............... 606/151, 155; 623/1.1, 1.11, 1.23
See application file for complete search history.

(56) References Cited

U.S. PATENT DOCUMENTS

| | | | |
|---|---|---|---|
| 3,657,744 A | 4/1972 | Ersek | 3/1 |
| 4,313,231 A | 2/1982 | Koyamada | 3/1.4 |
| 4,580,568 A | 4/1986 | Gianturco | 128/345 |
| 4,728,328 A | 3/1988 | Hughes et al. | 623/12 |
| 4,787,899 A | 11/1988 | Lazarus | 623/1 |
| 5,078,726 A | 1/1992 | Kreamer | 606/194 |
| 5,104,399 A | 4/1992 | Lazarus | 623/1 |
| 5,152,782 A | 10/1992 | Kowligi et al. | 623/1 |
| 5,275,622 A | 1/1994 | Lazarus et al. | 623/1 |
| 5,282,824 A | 2/1994 | Gianturco | 606/198 |
| 5,316,023 A | 5/1994 | Palmaz et al. | 128/898 |
| 5,330,490 A | 7/1994 | Wilk et al. | 606/153 |
| 5,360,443 A | 11/1994 | Barone et al. | 623/1 |
| 5,425,765 A | 6/1995 | Tiefenbrun et al. | 623/12 |
| 5,456,712 A | 10/1995 | Maginot | 623/1 |
| 5,476,506 A | 12/1995 | Lunn | 623/1 |
| 5,489,295 A | 2/1996 | Piplani et al. | 623/1 |
| 5,522,880 A | 6/1996 | Barone et al. | 623/1 |
| 5,522,881 A | 6/1996 | Lentz | 623/1 |
| 5,522,883 A | 6/1996 | Slater et al. | 623/1 |

(Continued)

FOREIGN PATENT DOCUMENTS

| | | |
|---|---|---|
| DE | 101 04 806 A1 | 8/2002 |
| FR | 2 768 921 A1 | 4/1999 |

(Continued)

*Primary Examiner* — Corrine M McDermott
*Assistant Examiner* — Christina Lauer
(74) *Attorney, Agent, or Firm* — Brinks Hofer Gilson & Lione

(57) ABSTRACT

A method for open surgical repair of a damaged portion of an artery or vein. A tubular medical assembly may include one or more shaped members, such as microbarbs, configured to anchor into the tunica intima and the tunica media of the vessel wall, and not to the tunic adventitia and vasa vasorum. The medical assembly is delivered to the damaged vessel portion via a delivery device through an open air pathway, and forms a conduit between transected ends of the damaged vessel.

16 Claims, 14 Drawing Sheets

(56) References Cited

U.S. PATENT DOCUMENTS

| | | | |
|---|---|---|---|
| 5,527,355 A | 6/1996 | Ahn | 623/1 |
| 5,562,728 A | 10/1996 | Lazarus et al. | 623/1 |
| 5,575,817 A | 11/1996 | Martin | 623/1 |
| 5,578,071 A | 11/1996 | Parodi | 623/1 |
| 5,578,072 A | 11/1996 | Barone et al. | 623/1 |
| 5,591,195 A | 1/1997 | Taheri et al. | 606/194 |
| 5,591,229 A | 1/1997 | Parodi | 623/1 |
| 5,628,783 A | 5/1997 | Quiachon et al. | 623/1 |
| 5,720,776 A | 2/1998 | Chuter et al. | 623/1 |
| 5,755,770 A | 5/1998 | Ravenscroft | 623/1 |
| 5,769,882 A | 6/1998 | Fogarty et al. | 623/1 |
| 5,800,526 A | 9/1998 | Anderson et al. | 623/1 |
| 5,824,040 A | 10/1998 | Cox et al. | 623/1 |
| 5,824,053 A | 10/1998 | Khosravi et al. | 623/1 |
| 5,843,173 A | 12/1998 | Shannon et al. | 623/1 |
| 5,984,955 A | 11/1999 | Wisselink | 623/1 |
| 6,110,198 A | 8/2000 | Fogarty et al. | 623/1.12 |
| 6,139,572 A | 10/2000 | Campbell et al. | 623/1.11 |
| 6,162,246 A | 12/2000 | Barone | 623/1.35 |
| 6,197,013 B1 | 3/2001 | Reed et al. | 604/509 |
| 6,267,783 B1 | 7/2001 | Letendre et al. | 623/1.13 |
| 6,306,164 B1 | 10/2001 | Kujawski | 623/1.35 |
| 6,315,792 B1 | 11/2001 | Armstrong et al. | 623/1.23 |
| 6,319,278 B1 | 11/2001 | Quinn | 623/1.13 |
| 6,352,553 B1 | 3/2002 | van der Burg et al. | 623/1.23 |
| 6,352,561 B1 | 3/2002 | Leopold et al. | 623/1.23 |
| 6,409,756 B1 | 6/2002 | Murphy | 623/1.35 |
| 6,432,131 B1 | 8/2002 | Ravenscroft | 623/1.13 |
| 6,451,051 B2 | 9/2002 | Drasler et al. | 623/1.15 |
| 6,517,570 B1 | 2/2003 | Lau et al. | 623/1.13 |
| 6,547,815 B2 | 4/2003 | Myers | 623/1.13 |
| 6,613,072 B2 | 9/2003 | Lau et al. | 623/1.11 |
| 6,663,667 B2 | 12/2003 | Dehdashtian et al. | 623/1.51 |
| 6,729,356 B1 | 5/2004 | Baker et al. | 139/387 R |
| 6,767,359 B2 | 7/2004 | Weadock | 623/1.14 |
| 6,770,087 B2 | 8/2004 | Layne et al. | 623/1.13 |
| 6,780,497 B1 | 8/2004 | Walter | 428/311.51 |
| 6,814,748 B1 | 11/2004 | Baker et al. | 623/1.14 |
| 6,852,122 B2 | 2/2005 | Rush | 623/1.13 |
| 6,878,164 B2 | 4/2005 | Kujawski et al. | 623/1.36 |
| 6,911,042 B2 | 6/2005 | Weadock | 623/1.23 |
| 6,949,119 B2 | 9/2005 | Myers | 623/1.13 |
| 7,044,961 B2 | 5/2006 | Lentz et al. | 623/1.13 |
| 7,044,962 B2 | 5/2006 | Elliott | 623/1.13 |
| 7,122,052 B2 | 10/2006 | Greenhalgh | 623/1.35 |
| 2002/0091439 A1 | 7/2002 | Baker et al. | 623/1.36 |
| 2002/0107535 A1 | 8/2002 | Wei et al. | 606/155 |
| 2003/0074055 A1 | 4/2003 | Haverkost | 623/1.16 |
| 2003/0120331 A1 | 6/2003 | Chobotov et al. | 623/1.13 |
| 2003/0158595 A1 | 8/2003 | Randall et al. | 623/1.13 |
| 2004/0044358 A1 | 3/2004 | Khosravi et al. | 606/194 |
| 2004/0098092 A1 | 5/2004 | Butaric et al. | 623/1.13 |
| 2004/0098096 A1 | 5/2004 | Eton | 623/1.13 |
| 2004/0106978 A1 | 6/2004 | Greenberg et al. | 623/1.13 |
| 2004/0193245 A1 | 9/2004 | Deem et al. | 623/1.13 |
| 2004/0199241 A1 | 10/2004 | Gravett et al. | 623/1.13 |
| 2004/0204753 A1 | 10/2004 | Shokoohi et al. | 623/1.16 |
| 2005/0021126 A1 | 1/2005 | Machan et al. | 623/1.13 |
| 2005/0033400 A1 | 2/2005 | Chuter | 623/1.11 |
| 2005/0038502 A1* | 2/2005 | Waysbeyn et al. | 623/1.23 |
| 2005/0049674 A1 | 3/2005 | Berra et al. | 623/1.13 |
| 2005/0070992 A1 | 3/2005 | Bolduc et al. | 623/1.15 |
| 2005/0080482 A1 | 4/2005 | Bonsignore | 623/1.35 |
| 2005/0090843 A1 | 4/2005 | Bolduc | 606/151 |
| 2005/0096737 A1 | 5/2005 | Shannon et al. | 623/1.44 |
| 2005/0154448 A1 | 7/2005 | Cully et al. | 623/1.15 |
| 2005/0171594 A1 | 8/2005 | Machan et al. | 623/1.13 |
| 2005/0187604 A1 | 8/2005 | Eells et al. | 623/1.13 |
| 2005/0240258 A1 | 10/2005 | Bolduc et al. | 623/1.27 |
| 2005/0240260 A1 | 10/2005 | Bolduc | 623/1.36 |
| 2005/0266042 A1 | 12/2005 | Tseng | 424/423 |
| 2005/0273155 A1 | 12/2005 | Bahler et al. | 623/1.13 |
| 2005/0288767 A1 | 12/2005 | Kujawski et al. | 623/1.13 |
| 2007/0027526 A1 | 2/2007 | Demetriades et al. | 623/1.13 |

FOREIGN PATENT DOCUMENTS

| | | |
|---|---|---|
| GB | 2 164 562 A | 3/1986 |
| WO | WO 96/39999 | 12/1996 |
| WO | WO 02/15823 A2 | 2/2002 |
| WO | WO 02/064355 A1 | 8/2002 |
| WO | WO 03/053288 A1 | 7/2003 |
| WO | WO 03/082152 A1 | 10/2003 |
| WO | WO 2004/006983 A2 | 1/2004 |
| WO | WO 2004/016201 A2 | 2/2004 |
| WO | WO 2005/048880 A2 | 6/2005 |

* cited by examiner

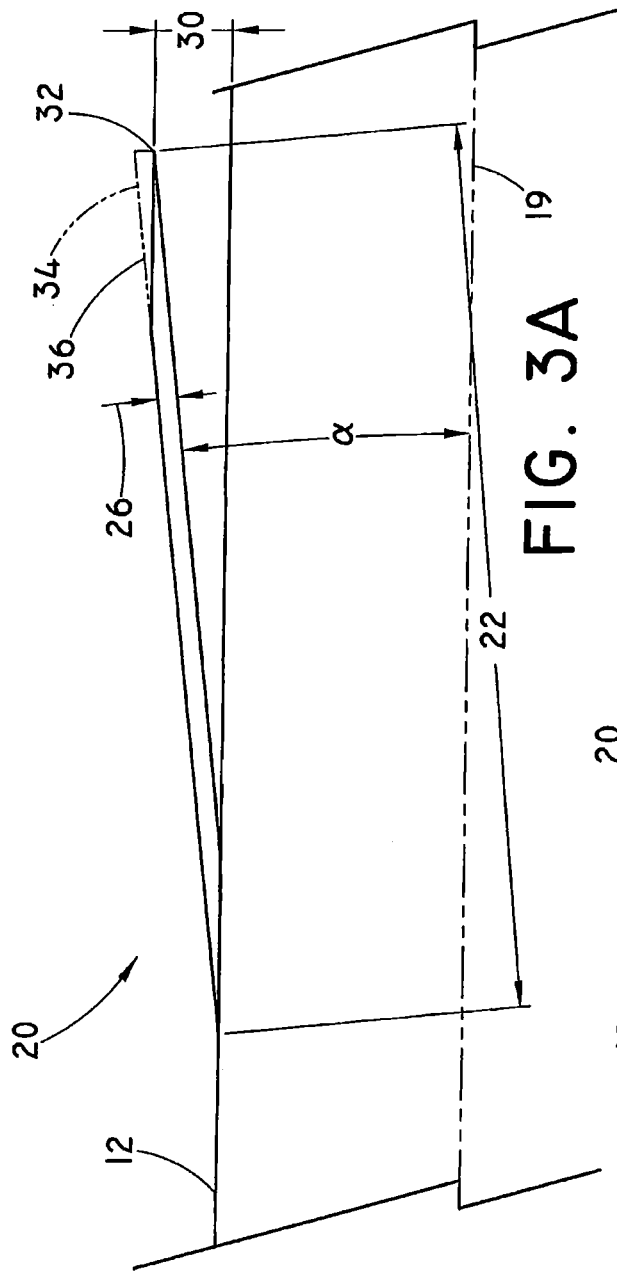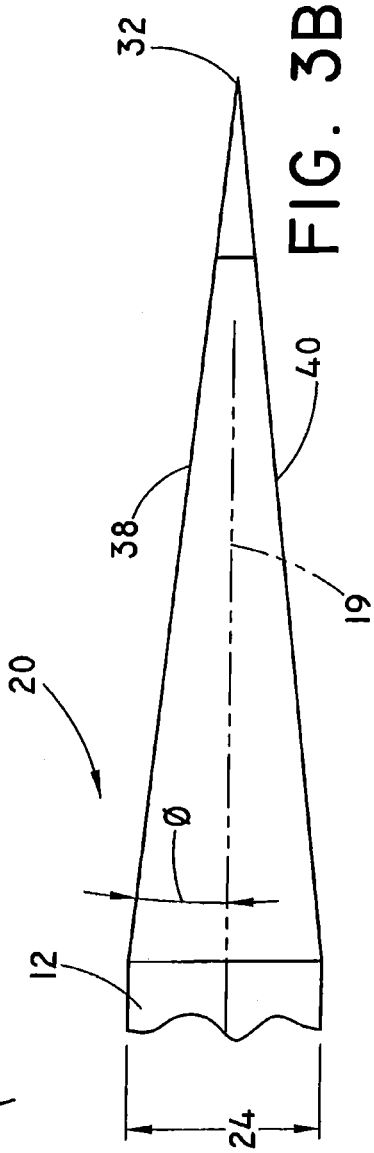

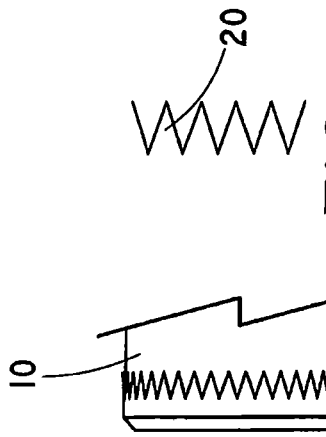
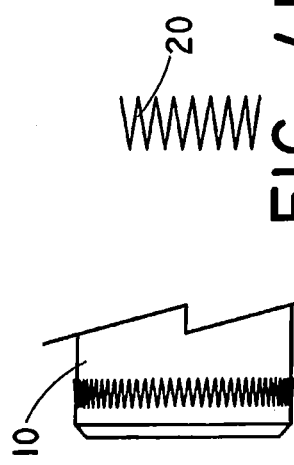
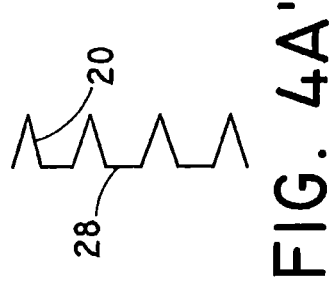
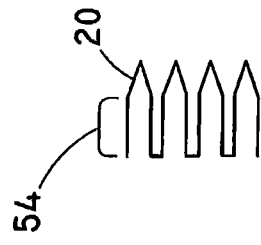
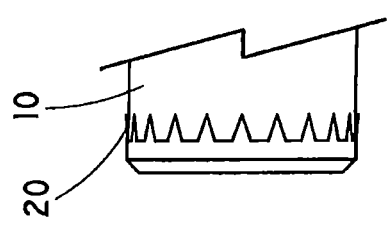

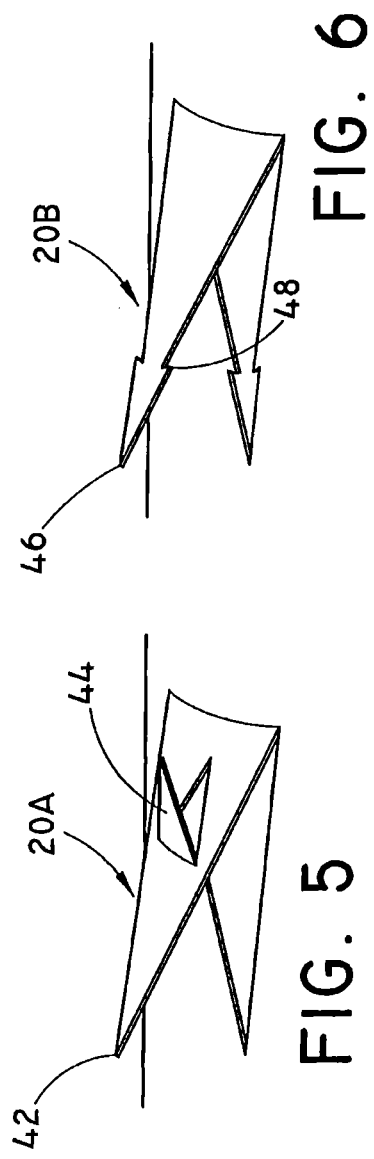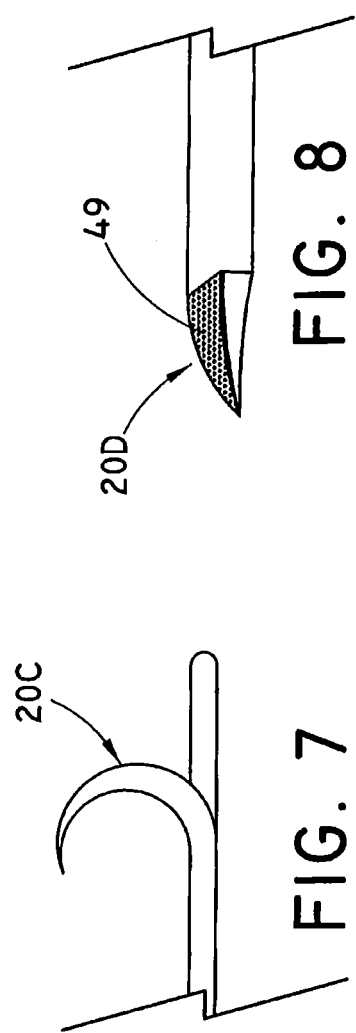

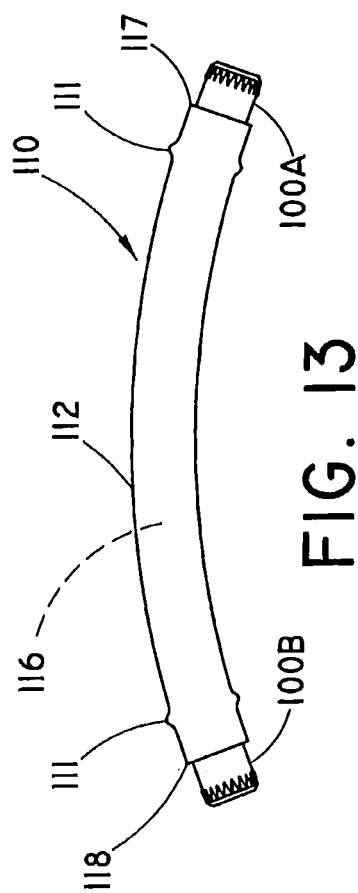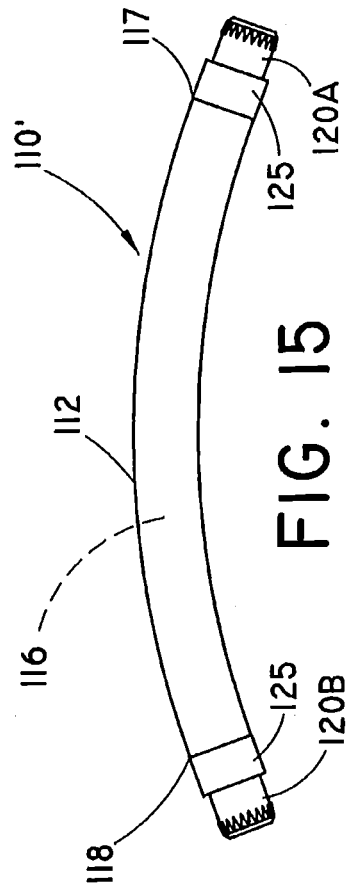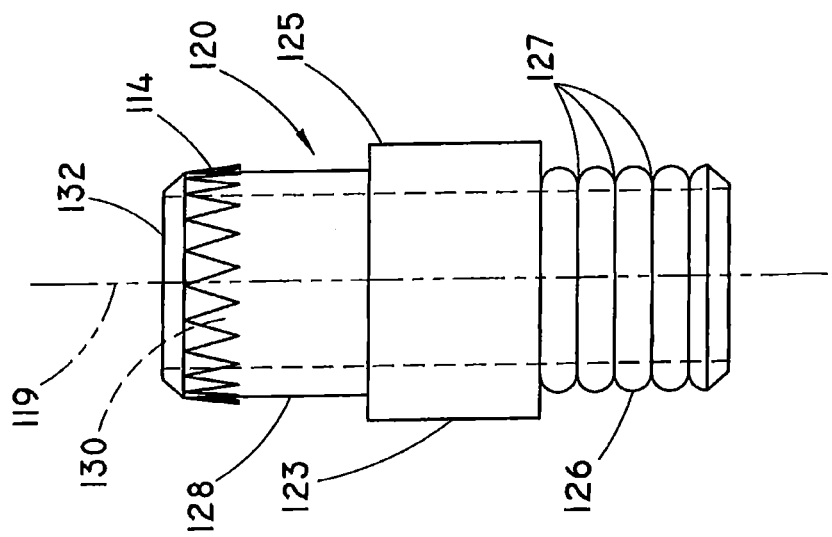

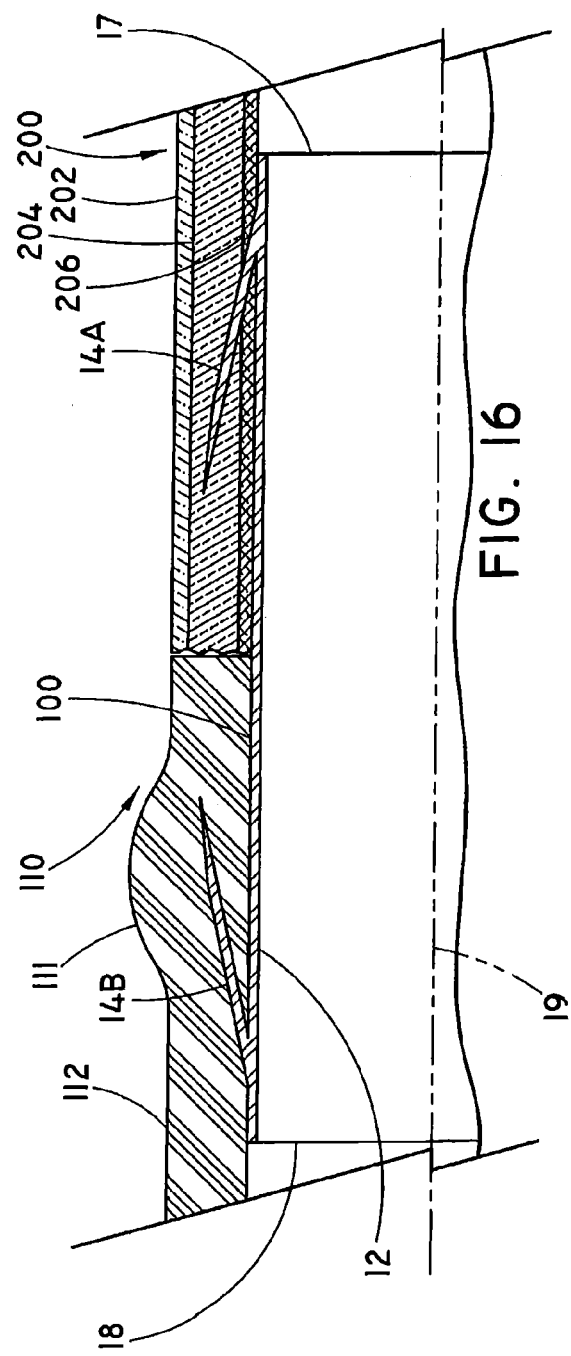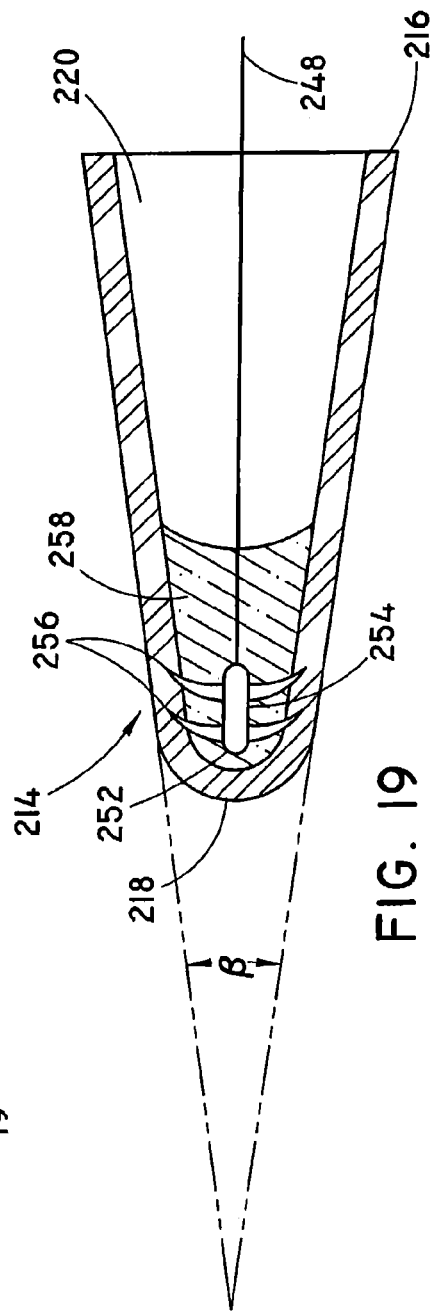

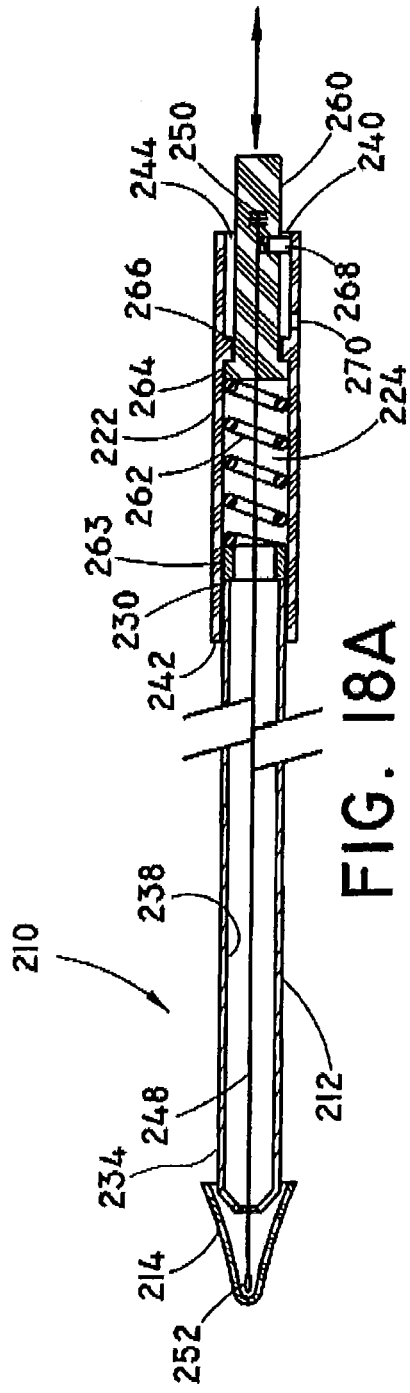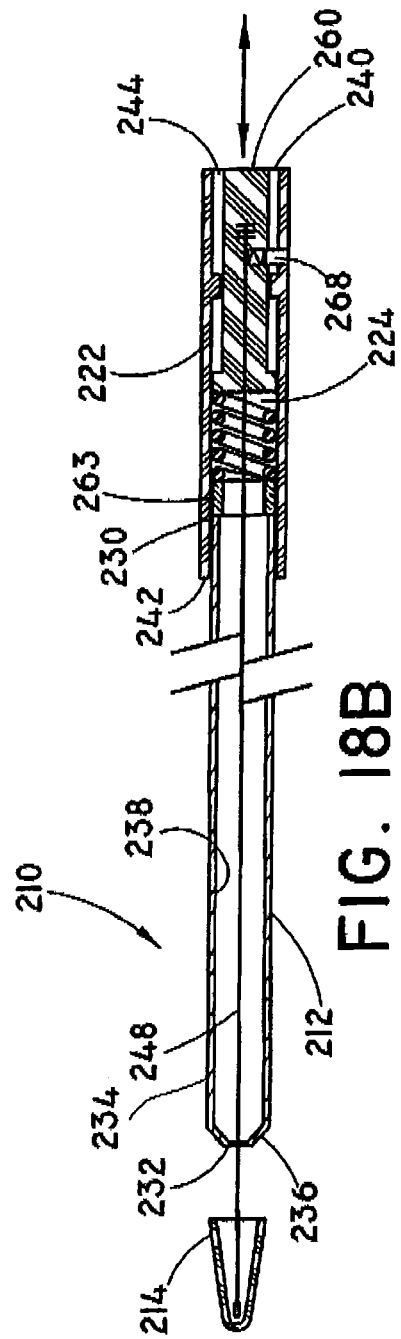

METHOD FOR OPEN SURGICAL PLACEMENT

RELATED APPLICATIONS

This application is a divisional of prior U.S. patent application Ser. No. 12/257,063, filed Oct. 23, 2008, now abandoned which claims priority and the benefit of provisional U.S. Patent Application Ser. No. 60/982,868, filed Oct. 26, 2007, and provisional U.S. Patent Application Ser. No. 61/127,308, filed May 12, 2008, all of which are hereby incorporated by reference in their entireties.

BACKGROUND

1. Technical Field

The present invention relates generally to a device and method for repair of body vessels. More particularly, the invention relates to a vascular conduit and method for repair of a damaged artery or vein during an emergency open surgical procedure.

2. Background Information

Emergency physicians frequently encounter patients having traumatic injury to a body vessel. Significant damage to a body vessel, such as a blood vessel, may expose a patient to deleterious conditions such as the loss of a limb, loss of function of a limb, increased risk of stroke, impairment of neurological functions, and compartment syndrome, among others. Particularly severe cases of vascular injury and blood loss may result in death. In such severe situations, the immediate goal is to obtain hemostasis while maintaining perfusion. Examples of treatments that are commonly performed by emergency physicians to treat vessel injury secondary to trauma include clamping the vessel with a hemostat, use of a balloon tamponade, ligation of the damaged vessel at or near the site of injury, or the insertion of one or more temporary shunts.

In the case of traumatic injury to blood vessels, the use of temporary shunts has been linked to the formation of clots. Shunts are generally placed as a temporary measure to restore blood flow, and to stop excessive blood loss. This may require returning the patient to the operating room for treatment and removal of the clots, often within about 36 to 48 hours of the original repair. When the patient has stabilized (generally a few days later), the shunt is typically removed and replaced with a vascular graft, such as a fabric graft that is sewn into place. Ligation of the damaged blood vessel may result in muscle necrosis, loss of muscle function, edema, or compartment syndrome with potential limb loss or death.

Due to the nature of the vascular injury that may be encountered, the use of shunts, repairing and/or ligating of a blood vessel often requires that such treatments be performed at great speed, and with a high degree of physician skill. Such treatments may occupy an undue amount of the time and attention of an emergency physician at a time when other pressing issues regarding the patient's treatment may also require immediate attention. In addition, since the level of particularized skill required may exceed that possessed by the typical emergency physician, particularly traumatic episodes may require the skills of a physician specially trained to address the particular trauma, such as a vascular trauma, and to stabilize the patient in the best manner possible under the circumstances of the case.

U.S. Patent Publication No. 2007/0027526 A1, incorporated by reference herein, discloses a device for repair of damaged portions of a body vessel. The device depicted in the patent publication includes a cylindrical body 12, having a fitting 14 disposed at either or both axial ends of the cylindrical body. This device is suitable for placement within a body vessel, such as a blood vessel, for repair of vascular trauma and restoration of fluid flow through the vessel. In the embodiment depicted in FIG. 3A of the patent publication, the fitting comprises an elongated tubular structure having a recessed portion 16 adjacent each axial end of a main fitting body portion 15, which may be compressed to secure the graft to the fitting. Alternatively, the graft can be secured by a slidable cuff received by a feature within the ring. One end of the fitting is snugly received within the lumen of the cylindrical body, and one or more sutures 18 are tied around the circumference of the cylindrical body to secure the fitting firmly to the cylindrical body. When the device is positioned in the vessel undergoing repair, one or more sutures 20 are tied around the vessel at an exposed portion of the fitting, as shown in FIG. 5, to secure the vessel to the fitting. The device depicted in the 2007/0027526 A1 publication is believed to be effective in repairing damaged vessels utilizing open surgical techniques in an emergency situation. However, since the device utilizes sutures to affix the damaged tissue portions to the fitting, the physician must take time to tie the sutures properly. Although in modern medicine sutures can be tied in relatively rapid fashion, any step in a repair process that occupies physician time in an emergency situation is potentially problematic. Therefore, efforts continue to develop techniques that reduce the physician time required for such techniques, so that this time can be spent on other potentially life-saving measures.

In addition to the foregoing, the use of sutures to affix the vessel to the fitting compresses the tissue of the vessel against the fitting. Compression of this tissue may result in necrosis of the portion of the vessel tissue on the side of the suture remote from the blood supply. Necrosis of this portion of the vessel tissue may result in the tissue separating at the point of the sutures. In this event, the connection between the vessel and the fitting may become weakened and subject to failure. If the connection fails, the device may disengage from the vessel.

U.S. Patent Publication No. 2005/0038502 A1, filed Apr. 21, 2004, describes a docking head that is mounted on a graft having an outer diameter so as to couple the graft to a blood vessel without requiring the use of sutures. The docking head includes a hollow truncated cone having a passage that is adapted to correspond to the outer diameter of a graft and a plurality of outwardly pointing and inclined barbs. The barbs may be flexible and inclined opposite a truncated end of the hollow truncated cone and are 1 to 4 times the thickness of the wall of the blood vessel. The inclined barbs are arranged at the circumference of the conical structure in at least one row and are distally pointed to the direction of the graft's body. In operation, the conical structure followed by the graft is inserted into neck through its narrow end while inclined barbs smoothly pass through a portion of the neck. Upon pulling back the conical structure, inclined barbs are embedded within the neck, forming a firm and sealed connection between the vessel and the graft.

While the outward facing barbs may facilitate secure placement of graft by securing the truncated cone portion within a body vessel, the particular design of the outward facing barbs presents drawbacks. First, these inclined barbs extending from the outer surface of the docking head, for example as shown in FIGS. 14 and 15, may engage body tissue away from the intended point of treatment during placement of the device. The tendency of the barbs pointing outwardly to engage tissue or other surfaces inadvertently can present a challenge during emplacement of the graft. Second, once in place within a body vessel, these barbs are not sized to penetrate an optimal distance into the wall of the body vessel. For example, FIG. 19 shows barbs 404 penetrating through the entire wall of a body vessel, which can lead to undesirable complications, such as bleeding and/or thrombus formation.

Thus, it would be desirable to provide a conduit and method for use in repair of a body vessel, such as an artery or a vein, and/or a delivery system, during emergency surgery in a manner that is time effective, that addresses the trauma at hand to the extent possible, and that utilizes techniques that may be readily practiced by an emergency physician. In addition, it would be desirable if the conduit utilized during emergency surgery is permanently placed within the patient, thereby obviating a need for subsequent surgical intervention. It is also desirable to utilize a medical device having inclined barbs that are shielded from inadvertent contact with body tissue by a delivery system during the delivery process, and/or barbs adapted to penetrate only a portion of the wall of the body vessel required to secure the medical device within the body vessel.

SUMMARY

In a first embodiment, a device for intraoperative repair of a damaged portion of a body vessel is provided. The device can be a vascular conduit for use in repair of the body vessel, such as an artery or a vein, during emergency surgery in a manner that is time effective, that addresses the trauma at hand to the extent possible, and that utilizes techniques that may be readily practiced by an emergency physician. The device utilized during emergency surgery can be permanently placed within the patient, thereby obviating a need for subsequent surgical intervention. Since the body vessel has a vessel wall including a tunica intima, a tunica media, and a tunica adventitia, the device controllably interacts with the tunica intima, basement membrane, and tunica media, and avoids any interaction with the tunica adventitia to not disrupt the vasa vasorum residing in the tunica adventitia. The device is preferably secured in a rapid manner without the use of a ligature or suture placed around the vessel, which may cause distal necrosis.

In one aspect, the device includes a tubular conduit having a wall defining a lumen about a longitudinal axis between a first axial end and a second axial end. The tubular conduit may include a flexible biocompatible material, such as expanded polytetrafluoroethylene, silicone, polyurethane, polyamide, or the like. The device also includes a first connector and a second connector disposed at the respective first and second axial ends of the tubular conduit. The first and second connectors can have a first portion engageable with the wall of the tubular conduit and a second portion having at least one shaped member extending radially therefrom. The shaped member can include barbs, fibers, bristles, or outer protruding and penetrable media. The shaped member can be dimensioned and arranged along the second portion to penetrate and anchor into the tunica intima and tunica media of the vessel wall upon insertion of the device into the body vessel. In one example of the device, the first portion of at least one of the first and second connectors has at least one shaped member, where the shaped member of the first portion is penetrable and anchorable into wall of the tubular conduit.

In another aspect of the device, the shaped member of the second portion and/or the first portion of the first and second connectors includes a plurality of microbarbs. The microbarbs can be spaced along a circumference of the second and/or first portion, and can be aligned at an acute angle relative to the longitudinal axis. In one example, the microbarb is aligned at an acute angle of about 5 degrees to about 30 degrees, and most preferably about 20 degrees to about 25 degrees, relative to the longitudinal axis. The microbarb can include a body having a first and second edge converging to form a tip region. A portion of the body of the microbarb outside the tip region may have a dullness configured to not cut or lacerate the body vessel radially when the microbarb is engaged. The tip region that can have a surface generally parallel relative to the longitudinal axis, and the surface may also be arcuate. The microbarbs can be arranged to be spaced along the circumference of the tubular body to form at least one ring of microbarbs. The microbarbs can be at various acute angles relative to the longitudinal axis, have various quantities along the circumference, various sizes, and/or a substantially parallel surface relative to the longitudinal axis.

In a second embodiment, a delivery system for deploying a tubular medical device in a body vessel. In one aspect, the delivery system can include an elongated tubular member that has a lumen about a longitudinal axis and a proximal end and a distal end. The elongated tubular member can be sized to extend through the lumen of the tubular medical device. A handle can be attached to the proximal end of the elongated tubular member. The handle has a lumen about the longitudinal axis and a proximal end and a distal end. The lumen of the handle is in communication with the lumen of the elongated tubular member. A dilator tip is disposed at the distal end of the elongated tubular member. The dilator tip can be sized and configured to receive the distal end of the elongated tubular member and to engage the distal end of the tubular medical device. The delivery may further include a controller disposed at the handle, which manipulates the dilator tip. The controller includes a control member extending through the lumens of the respective elongated tubular member and the handle. The control member can have a distal end attached to the dilator tip and a proximal end attached to the controller. The controller can be configured to retract the dilator tip in a proximal direction to a retracted position and to extend the dilator tip in a distal direction to an extended position.

In another aspect of the delivery system, the dilator tip has a conical shape tapering from a blunt distal end to a proximal end. The dilator tip preferably includes a cavity with a proximal region that can be sized and configured to receive the distal end of the elongated tubular member and to engage the distal end of the tubular medical device. In one example, the proximal region of the dilator tip may be configured to expand radially between a first cross-sectional area and a second cross-sectional area greater than the first cross-sectional area. The first cross-sectional area is less than a cross-sectional area of the lumen of the tubular medical device, while the second cross-sectional area is greater than the cross-sectional area of the lumen of the tubular medical device. In another example, the proximal region of the dilator tip can be configured to enclose partially the distal end of the tubular medical device when in the retracted position. The proximal region of the dilator tip may be configured to engage to the distal end of tubular medical device, or optionally, the proximal region may be configured to apply a radially compressive force to the distal end of the tubular medical device, when the dilator tip is in the retracted position, such that the tubular medical device can be retained in a fixed position. When the tubular medical device includes a shaped member, such as a plurality of microbarbs that are spaced along a circumference at the distal end of the tubular medical device, the proximal region of the dilator tip can be configured to enclose partially the microbarbs of the tubular medical device to protect the body vessel during deployment.

In yet another aspect of the delivery system, the controller is movable between a first position to retract the dilator tip to the retracted position and a second position to extend the dilator tip to the extended position. The controller may also include a spring mechanism disposed within the lumen of the handle. The spring mechanism can be biased to an expanded configuration to retain the controller at the first position and being moveable to a compressed configuration to move the controller to the second position. The controller can also include a lockable switch that is movable between a first position to allow the controller to move between the first and second positions and a second position to fix the controller at the second position.

In a third embodiment, a method of delivering a medical device system for intraoperative repair of a damaged portion of a body vessel having a vessel wall. Since during emergency surgery effective use of time of an emergency physician can be critical, the method can be performed in a manner that is time effective, that addresses the trauma at hand to the extent possible, and that utilizes techniques that may be readily practiced by the emergency physician. The medical device system can include a first connector and a second connector and a tubular conduit. The tubular conduit has a wall defining a lumen about a longitudinal axis between a first axial end and a second axial end. The first and second connectors are disposable with the respective first and second axial ends of the tubular conduit. The first and second connectors can have a first portion engageable with the wall of the tubular conduit and a second portion. The second portion can include at least one shaped member dimensioned and arranged along the second portion to penetrate and to anchor into the vessel wall of the body vessel. In one aspect, the body vessel can be transected or cut to form a first portion and a second portion of the body vessel. The transection can be at the damaged portion of the body vessel or can be just outside the damaged portion. Triangulation sutures can be attached proximate the ends of the first and second portions to keep the first and second portions fixed in place and to keep the vessel lumen opened for deployment of the medical device system. The first and second connectors of the medical device system can be deployed into the respective first and second portions of the body vessel with a delivery system. The tubular conduit can be engaged with the first connector and the second connector to form the medical device system to repair the damaged portion of the body vessel intraoperatively.

In another aspect of the method of delivery, the delivery system includes a dilator tip sized and configured to engage the at least one shaped member of the second portion of the respective first and second connectors. The dilator tip can be movable between a retracted position to engage with the at least one shaped member and an extended position to disengage from the at least one shaped member. Deploying the first and second connectors can include inserting the delivery system, with one of the first and second connectors loaded and the dilator tip in the retracted position, into the lumen of the respect first and second portion of the body vessel. Once positioned at a suitable site, the dilator tip can then be translated from the retracted position to the extended position to permit penetration and anchoring of the first and/or the second connector into the respective first and second portion of the wall of the body vessel. Other steps may include engaging the tubular conduit with the first connector before loading onto the delivery system. The first connector including the tubular conduit is then deployed in to the first portion of the body vessel with the delivery system. The second connector is deployed and then attached to the tubular conduit. The triangulation sutures can then removed.

The medical device system can be loaded onto the delivery system by inserting the dilator tip, in the extended position, through the lumen of the one of the first and second connectors, and the tubular conduit if already attached to the first connector. Once the dilator tip is extended past the distal end of one of the first and second connectors, the dilator tip can be moved from the extended position to the retracted position. In the retracted position, the dilator tip can engage with the at least one shaped member to prevent the respective first and second connector from translating during delivery.

BRIEF DESCRIPTIONS OF THE DRAWINGS

FIG. 3A is an elevation view of a microbarb of the vascular conduit.

FIG. 3B is a downward view of the microbarb of FIG. 3A.

FIG. 4A illustrates a microbarb configuration.

FIG. 4A' illustrates an enlarged view of the microbarbs of FIG. 4A.

FIG. 4B illustrates a microbarb configuration.

FIG. 4B' illustrates an enlarged view of the microbarbs of FIG. 4B.

FIG. 4C illustrates a microbarb configuration.

FIG. 4C' illustrates an enlarged view of the microbarbs of FIG. 4C.

FIG. 4D illustrates a microbarb configuration.

FIG. 4D' illustrates an enlarged view of the microbarbs of FIG. 4D.

FIG. 5 illustrates a bi-directional microbarb configuration.

FIG. 6 illustrates a bi-directional microbarb configuration.

FIG. 7 illustrates a curved microbarb configuration.

FIG. 8 illustrates a microbarb configuration.

Figure 9:
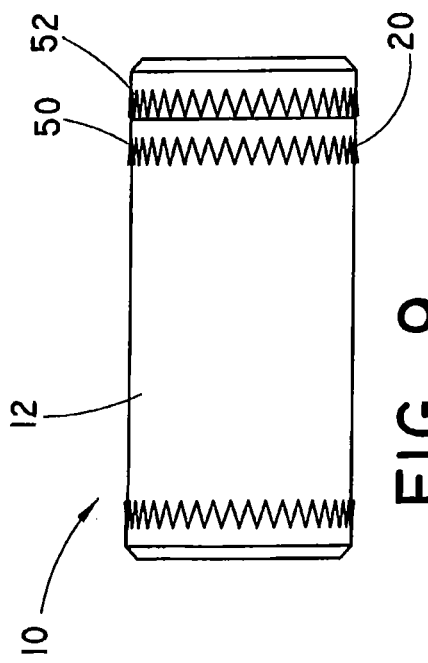

FIG. 9 illustrates a multi-ring microbarb configuration.

Figure 10:
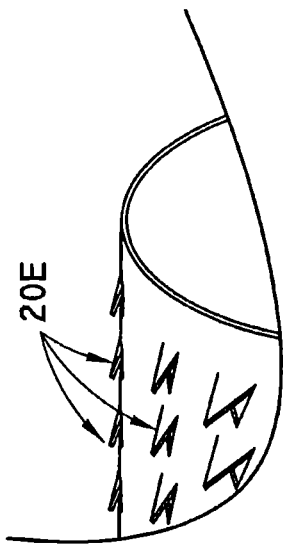

FIG. 10 illustrates a microbarb configuration.

Figure 11:
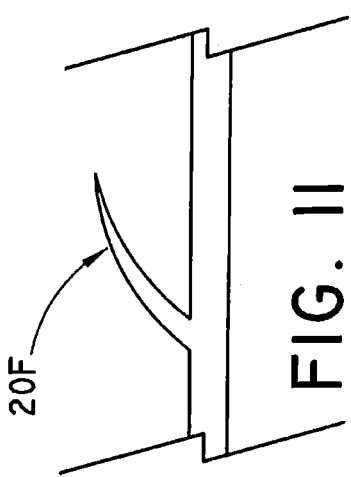

FIG. 11 illustrates a microbarb configuration of a shape memory composition in the open configuration.

Figure 12:
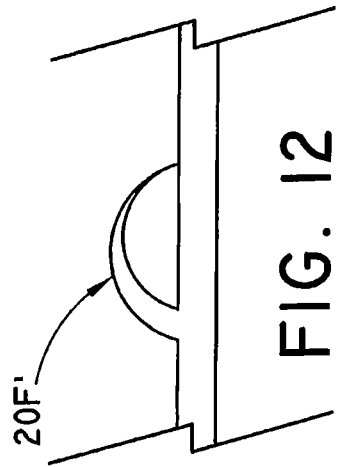

FIG. 12 illustrates a microbarb configuration of FIG. 11 in the closed configuration.

FIG. 13 is a perspective view of another vascular conduit for open surgical, or intraoperative, placement.

FIG. 14 shows an alternative connector configuration.

FIG. 15 is a perspective view of alternative vascular conduit for open surgical, or intraoperative, placement using the fitter of FIG. 14.

FIG. 16 is a side view depicting the vascular conduit engaged with the flexible tubular body and the body vessel.

Figure 17A:
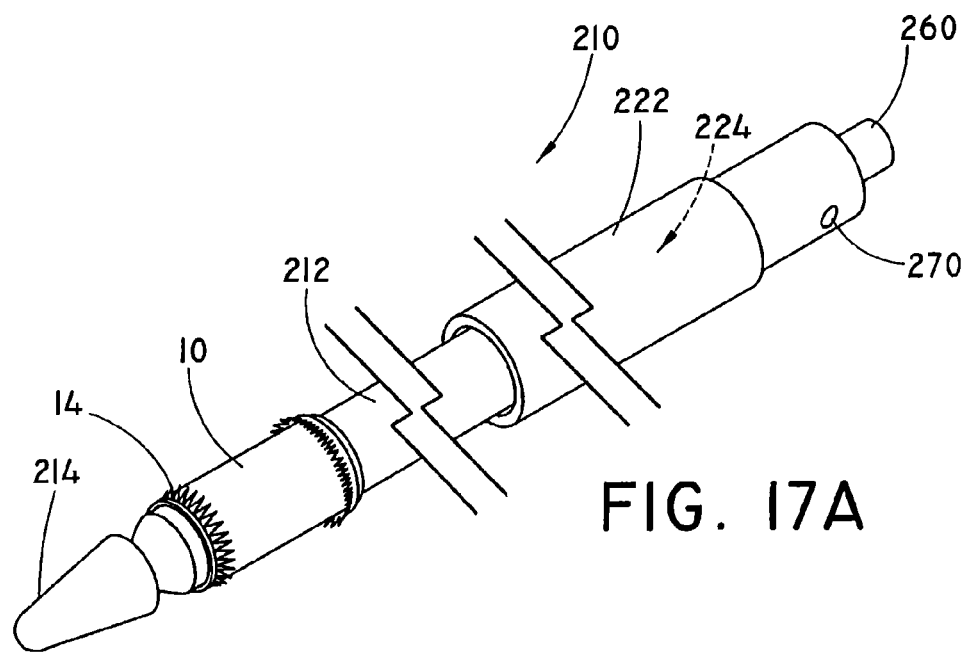

FIG. 17A is a perspective view of one embodiment of a delivery system.

Figure 17B:
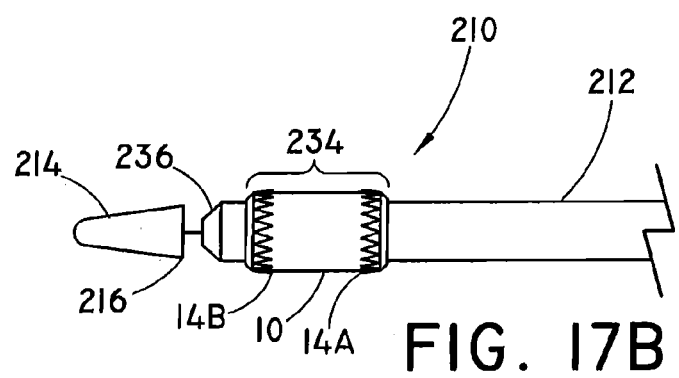

FIG. 17B is a side view of a delivery system with an extended dilator tip.

Figure 17C:
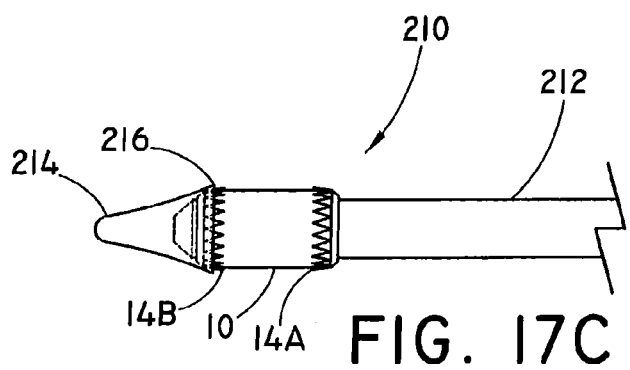

FIG. 17C is a side view of a delivery system with a retracted dilator tip.

FIG. 18A is a cross-sectional view of the delivery system of FIG. 17A with a retracted dilator tip.

FIG. 18B is a cross-sectional view of the delivery system of FIG. 17A with an extended dilator tip.

FIG. 19 is a cross-sectional view of a dilator tip of a delivery system.

Figure 20A:
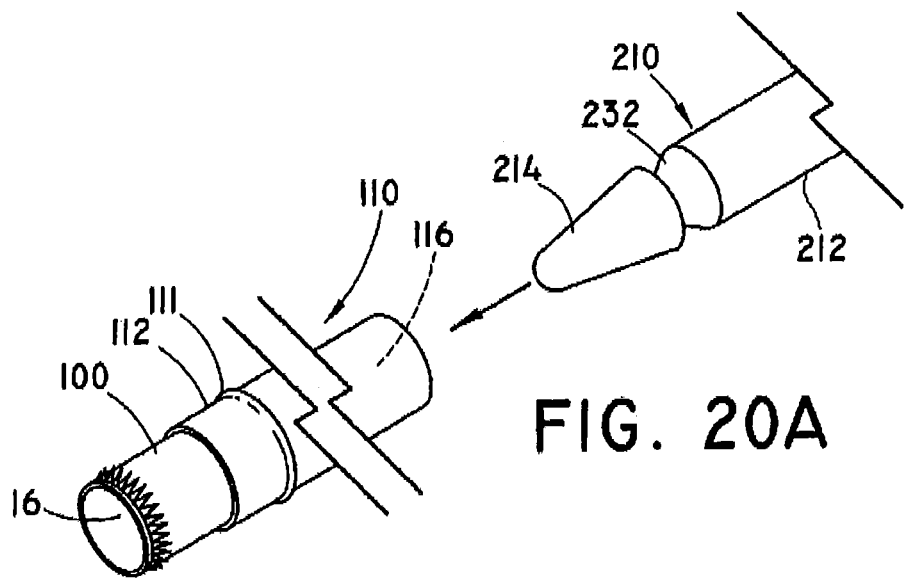

FIG. 20A is a perspective view of loading a vascular conduit onto a delivery system.

Figure 20B:
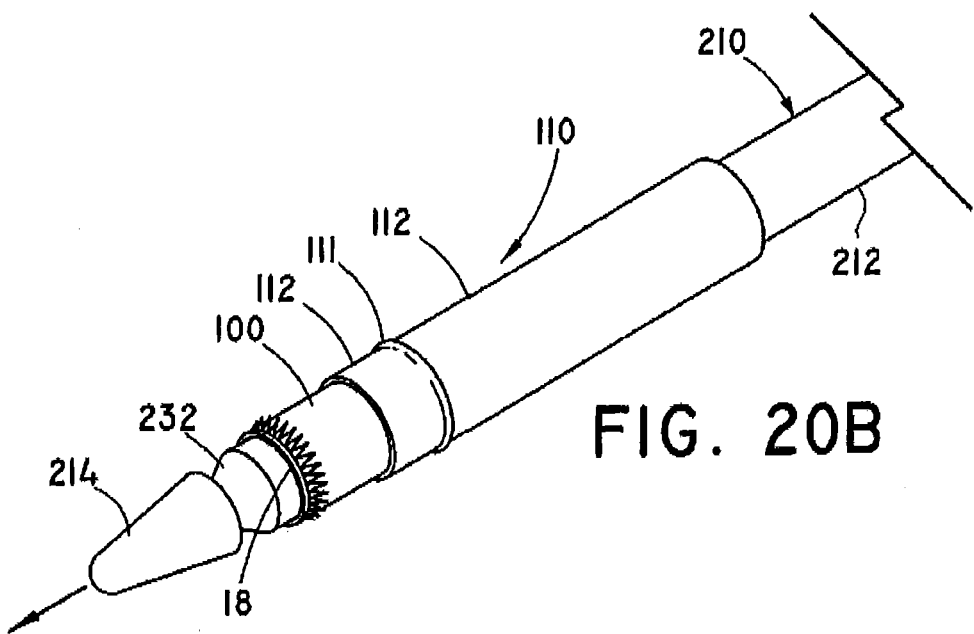

FIG. 20B is a perspective view of loading the vascular conduit onto the delivery system of FIG. 20A.

Figure 21A:
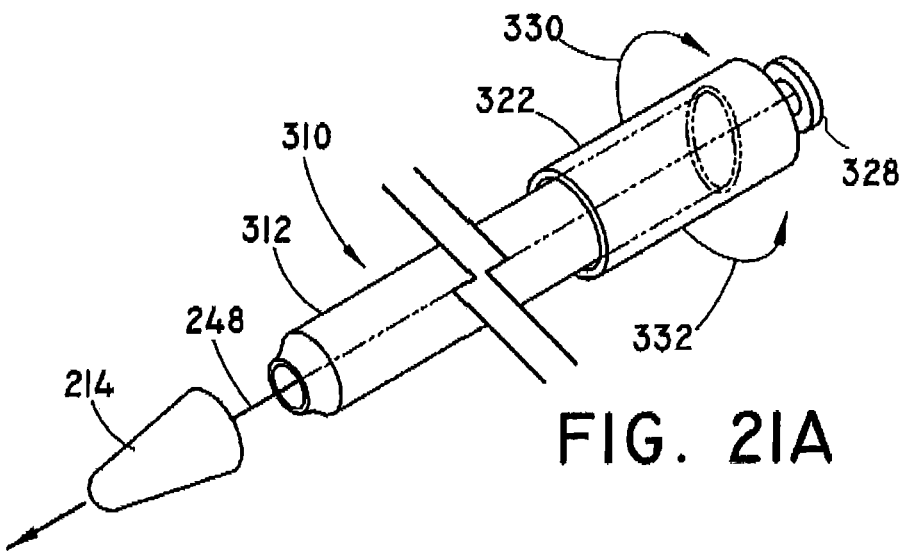

FIG. 21A is a perspective view of another embodiment of a delivery system.

Figure 21B:
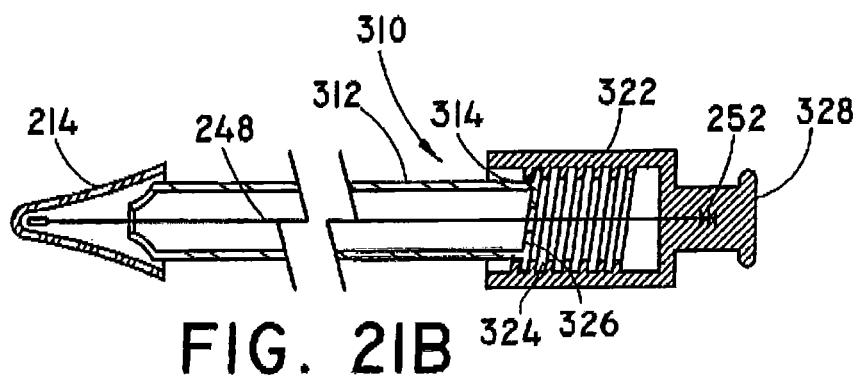

FIG. 21B is a cross-sectional view of the delivery system of FIG. 21A.

Figure 22:
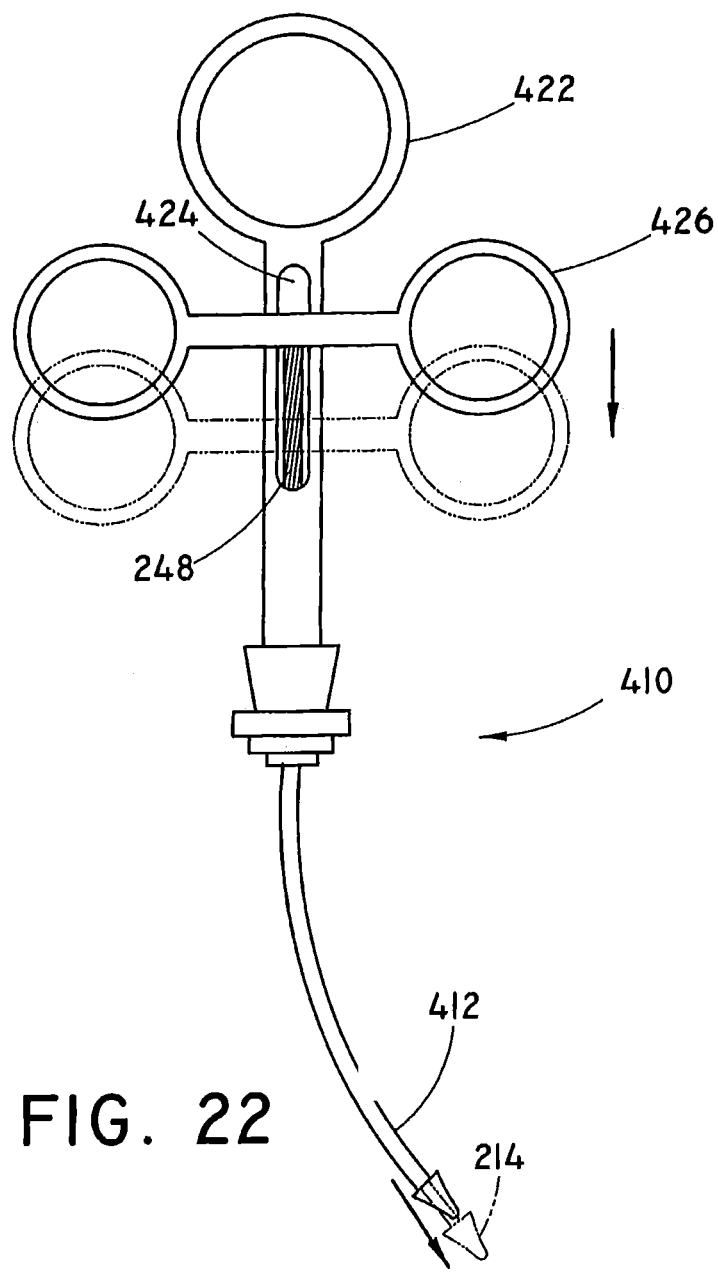

FIG. 22 is a perspective view of another embodiment of a delivery system.

Figure 23A:
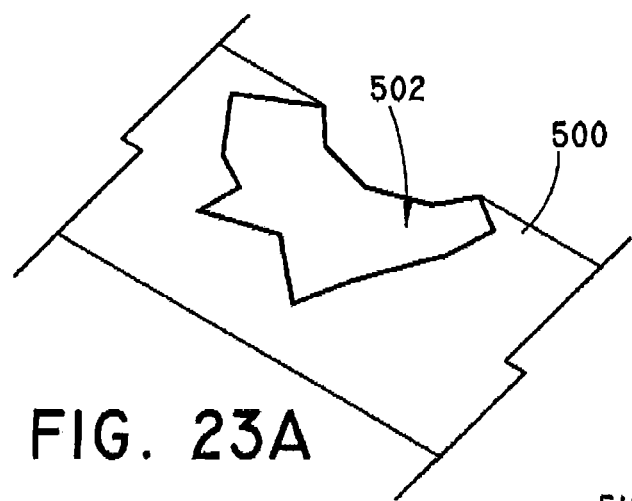

FIG. 23A illustrates a blood vessel that has been previously been subjected to a traumatic episode.

Figure 23B:
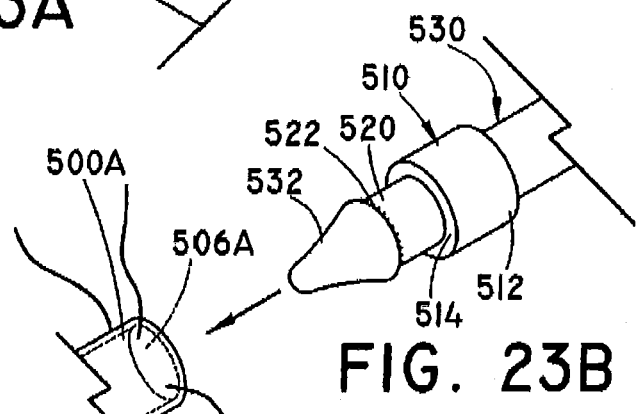

FIG. 23B illustrates a step during a method of implanting a vascular conduit within the blood vessel of FIG. 23A.

Figure 23C:
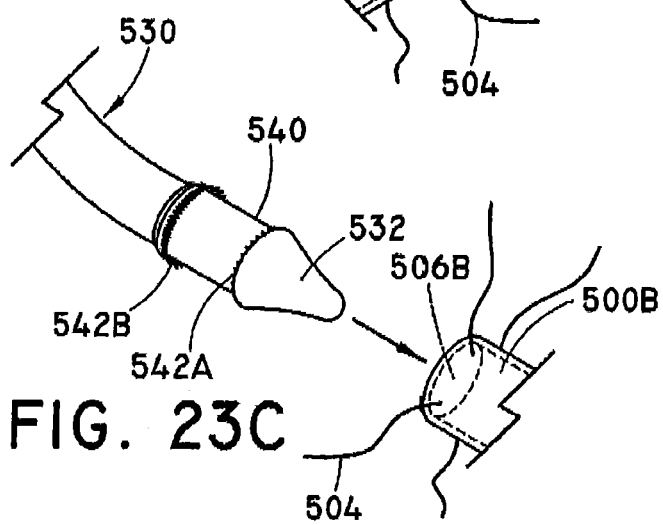

FIG. 23C illustrates a step during a method of implanting a vascular conduit within the blood vessel of FIG. 23A.

Figure 23D:
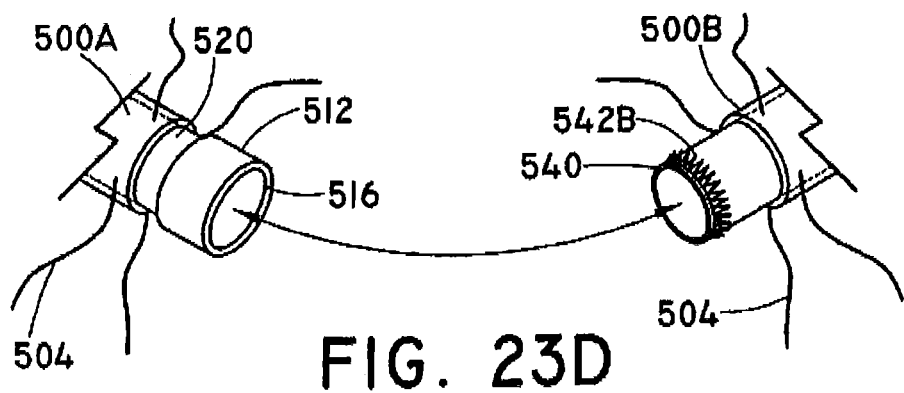

FIG. 23D illustrates a step during a method of implanting a vascular conduit within the blood vessel of FIG. 23A.

Figure 23E:
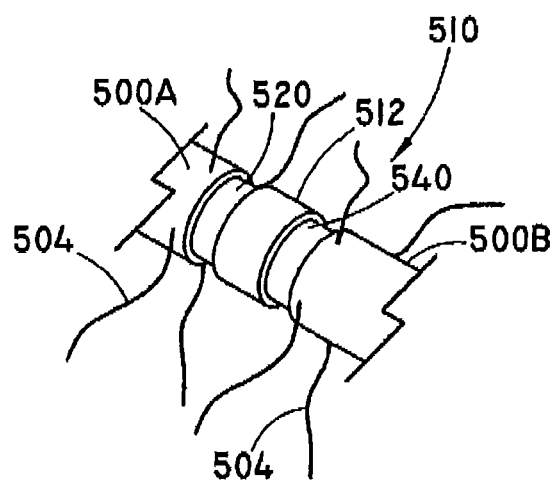

FIG. 23E illustrates a step during a method of implanting a vascular conduit within the blood vessel of FIG. 23A.

DETAILED DESCRIPTION OF THE DRAWINGS AND THE PRESENTLY PREFERRED EMBODIMENTS

For the purposes of promoting an understanding of the principles of the invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The device of the present invention is useful for repair of a body vessel, such as a blood vessel, during an emergency open surgical procedure. The device is particularly useful for repair of a transected artery or vein during emergency surgery, and particularly, to obtain hemostasis while maintaining blood perfusion.

Trauma surgeons and staff are often faced with victims who have been injured by gunshots, knife wounds, motor vehicle accidents, explosions, etc. Such patients can only survive such wounds by maintaining adequate blood flow to critical organs, such as the brain, liver, kidneys, and heart. Conventional surgical repair is generally difficult with such actively bleeding, moribund patients. In many instances, there is simply not enough time to repair the vessels adequately by re-approximating and suturing the transected vessels. In many situations, surgeons will simply insert a temporary shunt (such as a Pruitt-Inahara Shunt) into the vessel. If the patient survives the initial trauma, after 24-48 hours, the temporary shunt may be removed, and further surgical interventional and vessel repair would follow. With the inventive device, the emergency surgical repair is permanent, thereby obviating the need for further surgical intervention and repair.

In order to understand the structure and operation of the inventive device, a brief description of the structure of a blood vessel in the body is helpful. Blood vessels are of two types, namely arteries and veins. Generally speaking, arteries are elastic vessels that carry oxygenated blood away from the heart, and veins are elastic vessels that transport blood to the heart for transport to the lungs for oxygenation. The walls of both arteries and veins are formed to have three layers, or tunics. The inner layer is referred to as the tunica intima, which is composed of endothelium and delicate collagenous tissue. The middle layer is referred to as the tunica media, which is composed of typically a muscular layer, and consists of smooth muscle and elastic fibers. The outer layer is referred to as the tunica adventitia, which is the outer covering of the vessel, and is composed of connective tissue, collagen, and elastic fibers. The tunic adventitia includes small vessels, referred to as vasa vasorum, which supply nutrients to the tissue.

Figure 1:
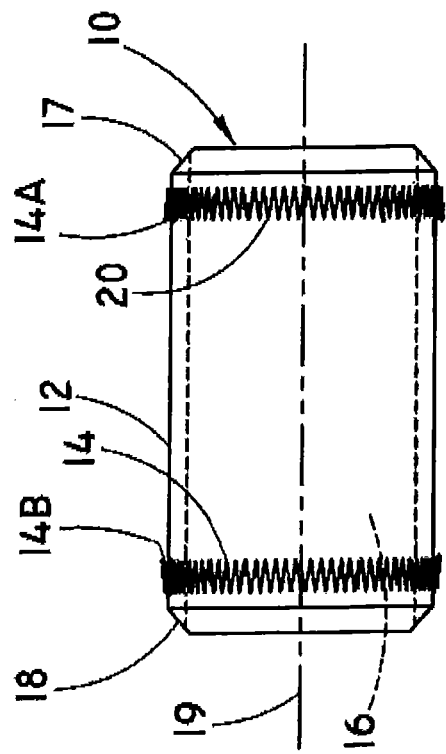
FIG. 1 is a sectional view of a blood vessel that schematically illustrates the orientation of the layers of the blood vessel.

FIG. 1 is a sectional view of a blood vessel 1 that schematically illustrates the orientation of these layers. Vessel 1 includes a lumen 2 extending therethrough for transport of blood. The respective tunica intima 4, tunica media 6, and tunica adventitia 8 extend radially outwardly from the lumen 2. The tunica intima 4 includes a thin layer of connective tissue 5 (often referred to as the basement membrane) in the region where it joins the tunica media 6. A thin layer of internal elastic lamina 7 may also be found between the tunica intima 4 and the tunica media 6. Another thin layer of external elastic lamina 9 may also be found between the tunica media 6 and the tunic adventitia 8. The illustration and accompanying explanation provided hereinabove is only intended to be a very brief explanation of the structure of a blood vessel. Those skilled in the art will appreciate that the relative thickness of a particular layer will vary from that shown schematically in FIG. 1, and that the thickness of various layers will also vary depending upon whether the vessel is an artery or a vein. In each instance however, the vein will include the three layers illustrated in FIG. 1. It is believed that those skilled in the art will have sufficient appreciation for the basic vessel structure that further explanation is unnecessary to achieve an understanding of the present invention.

The invention is primarily described herein with reference to one of its intended uses, that being for open surgical repair of a blood vessel. However, those skilled in the art will appreciate that the invention is also useful for repair, anchoring, and/or joinder of other body structures and vessels (e.g. joinder of ureter ducts or any body duct or channel).

It is noted that the microbarbs in the Figures are enlarged in order to illustrate the general shape of the microbarbs and do not accurately reflect the true size of the microbarbs in relation to the vascular conduit or connector.

Figure 2:
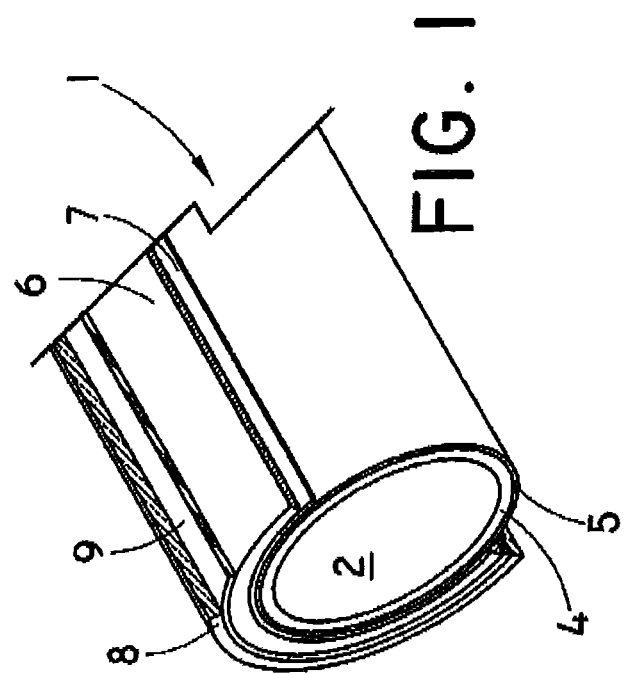
FIG. 2 is an elevation view of one embodiment of an inventive vascular conduit for open surgical, or intraoperative, placement.

FIG. 2 illustrates one embodiment of an inventive vascular conduit 10 for open surgical, or intraoperative, placement. In this embodiment, the vascular conduit 10 comprises a generally cylindrical body 12, having an anchoring means 14 on at least one axial end of the cylindrical body 12. The vascular conduit 10 has a size and shape suitable for placement within a body vessel, such as a blood vessel (either an artery or vein), and most particularly, for placement at the site of a vascular trauma.

The generally cylindrical body 12 generally comprises a hollow, elongated, biocompatible material having a lumen 16 extending therethrough between a distal end 17 and a proximal end 18 along a longitudinal axis 19. The cylindrical body 12 may be machined in a manner that allows for extremely precise diameter matching with the vessel, such that there is minimal separation or gap between the cylindrical body 12 and the vessel to avoid accommodating blood stagnation and thrombus accumulation. The cylindrical body 12 can have a substantially circular cross-section having an outer diameter suitably sized depending on the cross-sectional area and diameter of the vessel, such as about 4 mm or less to about 12 mm or more, to engage a substantial portion of the luminal surface of the body vessel. Although a substantially circular cross-section is preferable, the cross-section of the cylindrical body 12 may be elliptical or other shapes known to be used in a vessel in the body by one skilled in the art. Preferred dimensions of the cylindrical body 12 include 5 mm (0.197") thru 6 mm (0.236") ID. Larger diameters, e.g., 7 mm (0.276") and 8 mm (0.315"), may also be acceptable. The wall thickness of the cylindrical body 12 is typically 0.15-0.25 mm and should be suitable to support the vessel structurally and to permit sufficient blood flow through the lumen 16. The general length of the cylindrical body 12 will depend upon the size of the opening or puncture in the vessel. The length of the cylindrical body 12 can be at least as long as the opening in the vessel, if not longer, in order for the anchoring means 14 to penetrate and engage securably to an uncompromised portion of the vessel.

The biocompatible material of the cylindrical body 12 can be a relatively rigid structure, such as a metal, metal alloy, or a high-strength polymer. Optionally, a thin layer of PTFE or other biocompatible material can line the luminal surface of the cylindrical body 12. Generally, any biocompatible composition having the requisite strength may be utilized, as long as the composition has sufficient strength to maintain its relative dimension in use. The biocompatible material of the cylindrical body 12 can include stainless steel, PTFE, shape memory materials, such as nitinol, as well as compositions that are visible under common medical imaging techniques such as magnetic resonance imaging (MRI). One non-limiting example of a preferred composition that is visible under imaging techniques is titanium. The cylindrical body 12 can be formed from conventional materials well-known in the medical arts.

The presence of the anchoring means 14 permits the vascular conduit 10 to be secured to the tissue of the vessel upon insertion during an open surgical procedure. In particular, the anchoring means 14 provide vessel fixation while avoiding adverse conditions associated with disturbing the vasa vasorum and/or pressure induced necrosis of the medium muscular arteries of the type that may result from tying ligatures circumferentially around a connector or a vascular conduit. The anchoring means 14 can include various shaped member structures including, barbs, fibers, bristles, or outer protruding and penetrable media. One preferred anchoring means 14 is microbarbs 20, although some of the features discussed below relative to the microbarbs 20 may also be attributed to other types of anchoring means 14.

The mircrobarbs 20 can be sized and shaped in any manner to enable a secure connection with the vessel to inhibit migration of the vascular conduit 10 within the vessel. It is desirable, however, that the microbarbs 20 are sized and shaped such that they penetrate tunica intima 4, the basement membrane 5, and partially enter the tunica media 6 (FIG. 1). It is preferable that the microbarbs 20 do not enter the tunica adventitia, and more importantly, do not disturb or otherwise adversely affect the vasa vasorum. A fibrotic response can be created within the penetrated portions of the blood vessel, which further anchors the vascular conduit 10 in the vessel over time.

A wide variety of configurations for the microbarbs 20 are provided in order to better secure the vascular conduit 10 with the tissue. The microbarbs can be constructed to have varying dimensions, such as length, base width, thickness, barb angle, orientation, distribution, sharpness and point (tip) configuration, to optimize the manner and degree of penetration into the vessel wall, and preferably, to restrict penetration to only the tunica intima and partial tunica media layers as described. For example, the microbarbs 20 may be configured to penetrate the wall of the body vessel without cutting through the body vessel. In other examples, the microbarbs 20 are also configured to seat within the body vessel wall securely as to not further propagate or cut radially once engaged.

Referring to FIGS. 3A and 3B, the general microbarb length 22, angle, base width 24 and thickness 26 can vary depending on the vessel type and characteristics. For example, for a vascular conduit 10 having an outer diameter of 6 mm, the microbarbs 20 can have a length 22 in the range between about 0.1 mm to 1 mm, and preferably about 1 mm. The base width 24 of the microbarbs 20 typically depend on the number of microbarbs 20 positioned around the circumference of the cylindrical body 12. The number of microbarbs 20 can have a range from about 20 to about 80, although any number suitable for implantation of the vascular conduit is within the scope. As a result, the width 24 of the microbarbs 20 can vary between about 0.2 mm or less to about 0.4 mm or more. In some embodiments, there are no gaps between adjacent microbarbs, as shown in FIGS. 4B and 4D, and yet in other embodiments there are gaps 28 in between adjacent microbarbs having a gap length between about 0.2 mm to about 0.4 mm, or more or less depending on the circumstances, as shown in FIG. 4A. The arrangement without gaps between adjacent microbarbs may inhibit seepage of blood due to the activation of the clotting cascade in the localized area around the microbarbs 20. It can be appreciate by one skilled in the art to have some adjacent microbarbs without gaps and some adjacent microbarbs with gaps 28. In addition, a material such as collagen may be added around the circumference of the microbarbed connector to add an additional hemostatic component to the device.

Referring to FIG. 3A, the angle $\alpha$ of the microbarbs 20, in relation to the longitudinal axis 19, is preferably selected to orient the microbarbs 20 radially outward away from the longitudinal axis 19 in a manner to prevent penetration into the tunica adventitia. Optionally, the microbarbs 20 may be configured to penetrate at a certain depth 30 into the vessel wall as to avoid the tunic adventitia. Although it is preferable that all the microbarbs 20 have a substantially similar angle $\alpha$, or similar depth 30 penetration, it can be appreciated by one skilled in the art that microbarbs 20 having varying angles, or depth 30 penetrations, may be advantageous. Angles $\alpha$ of about 5 degrees to about 30 degrees are preferred, although angles $\alpha$ of up to about 45 degrees to 60 degrees may also be used in some applications depending on the length 22 of the microbarb and the preferred depth 30 penetration. For example, the angle $\alpha$ of the microbarbs 20 may be oriented at about 20 degrees to about 25 degrees, and most preferably at 23 degrees. The suitable length and angle and/or depth penetration can be determined by the vessel type and other considerations taking into account by one of ordinary skill in the art.

The tip 32 of the microbarbs 20 may be formed by one or more angled cuts to create a bi-angled tip, as shown in FIG. 3B. The cuts may form the body having edges 38, 40 having a similar angle $\Theta$. The angle $\Theta$ may range from about 15 degrees to about 60 degrees relative to the longitudinal axis 19, although the angle $\Theta$ for one edge of the edges 38, 40 can be substantially parallel to the longitudinal axis 19. The edges 38, 40 can be rounded or made dull to decrease the risk of the edges radially cutting the body vessel tissue once engaged. The edges 38, 40 can be cut by laser cutting and rounded by abrasive treatment, chemical treatment, abrasive blasting, and/or electropolishing or the like to create the dullness. It is preferred to have a tip 32 with a complex-angle, where, when the microbarb 20 is angled at a predetermined angle $\alpha$, the tip 32 is machined to remove a portion 34, represented by the dashed lines, and to create a surface 36 generally parallel to the longitudinal axis 19, as shown in FIG. 3A. Although the removed portion 34 is shown to be at the outward surface of the tip 32, the inner surface of the tip 32 can instead be machined to create a surface generally parallel. Alternatively, the surface 36 may be arcuate after being machined, being concave outwardly or inwardly depending on which side of the tip is machined. This can allow the tip 32 of the microbarbs 20 to be sharpened without sharpening the edges 38, 40 along the length of the microbarbs 20. Optionally, instead of removing the portion 34, a distal portion may be formed by cutting the microbarb 20 with a bent portion at the tip 32, or by bending the microbarb 20 at the tip 32, to create a surface or portion that is substantially parallel to the longitudinal axis 19. The surface 36 or bent potion may allow for easier penetration into the wall of the vessel to a limited depth 30 or distance into the innermost layer(s) of the body vessel wall, without passing through the body vessel.

The microbarbs 20 can be configured and oriented to grasp tissue in one direction, or in more than one direction. FIG. 3B illustrates a unidirectional microbarb. FIG. 5 illustrates a bi-directional microbarb 20A. In this arrangement, a first microbarb segment 42 extends in one direction, and a second microbarb segment 44 extends in another direction, such as the reverse direction. This type of microbarb 20A may be particularly effective for use with a spring-type deployment, as when the cylindrical body 12 comprises an expandable structure, such as a stent, which is either self-expanding or balloon expandable, which is discussed below. FIG. 6 illustrates another arrangement of a bi-directional microbarb 20B. In this arrangement, a first microbarb segment 46 extends in one direction, and a second microbarb segment 48 extends in the reverse direction, forming an arrow-like tip. FIG. 7 illustrates another microbarb arrangement with a curvature.

FIG. 8 illustrates another embodiment of the microbarbs 20D having a region 49 with a controlled porosity to allow for tissue in-growth as well as delivery of drugs or growth factors and other tissue modulators. For example, collagen-based formulations can be used to provide a growth and attachment matrix. There can also be features (e.g., bioremodelable materials, such as SIS) placed strategically around the cylindrical body 12 and/or microbarbs 20 of the vascular conduit 10 to promote tissue attachment.

The microbarbs 20 can be distributed along all or part of the circumference of cylindrical body 12 in an orderly, or a random, fashion. In the non-limiting embodiment shown in FIG. 2, the microbarbs 20 are provided on a ring-like structure positioned or formed at the distal and proximal ends 17, 18 of the cylindrical body 12 of the vascular conduit 10. As illustrated in FIG. 9, the vascular conduit 10 can include two rings 50, 52 of barbs 20, spaced axially at a suitable distance along the cylindrical body 12 of the vascular conduit 10. In other examples, the vascular conduit 10 may include different number of rings at each end of the cylindrical body 12. Utilizing a plurality of rings of microbarbs 20 may provide enhanced gripping to the vessel. In the embodiment shown, the microbarbs 20 of one of the rings need not have the same dimensions as the microbarbs 20 of the other ring. The microbarbs 20 need not be oriented and aligned along a ring as shown, and any arrangement may be substituted for that shown.

FIGS. 4A-D and FIGS. 4A'-D', illustrate other non-limiting microbarb configurations for the vascular conduit having a 6 mm outer diameter. FIGS. 4A and 4A' illustrate the vascular conduit 10 having twenty microbarbs 20 circumferentially, equally spaced, with the gaps 28 between adjacent microbarbs. FIGS. 4B and 4B' illustrate the vascular conduit 10 having fifty microbarbs 20 circumferentially, equally spaced, with no gaps between adjacent microbarbs. FIGS. 4C and 4C' illustrate the vascular conduit 10 having fifty microbarbs 20 circumferentially, equally spaced, with no gaps between adjacent microbarbs and with the microbarbs 20 having an extended linear portion 54 to make the microbarbs have a longer body. FIGS. 4D and 4D' illustrate the vascular conduit 10 having eighty microbarbs 20 circumferentially, equally spaced, with no gaps between adjacent microbarbs. Preferred configurations of microbarbs 20 can be measured in terms of maximum load and maximum extension at maximum load with under an axial tensile test. One such test includes affixing one end of a flexible vascular conduit having at 6 mm (0.24 inch) outer diameter and a 5.5 mm (0.216 inch) inner diameter and anchoring one connector to the vascular conduit. A general tensile rate of 12.7 cm/minute (5 inches/minute) is applied to one of the ends while measuring the tensile load and extension from the position from start of test to position at maximum load. Taking the configurations in FIGS. 4A-4D, the maximum tensile load measured in the range of about 1.1 to about 5.1 N (2.4±1.6 N) and the extension at maximum tensile load measured in the range of 13.8 mm to about 42.7 mm (27.2±12.7 mm).

Those skilled in the art are well aware of suitable means for fabricating structures having a desired size and shape, such as microbarbs 20, from substrate structures, such as a cylindrical body or ring of biocompatible material, or alternatively, for incorporating a microbarbs into a cylindrical body. Preferably, the microbarbs are made of a rigid material. One particularly favored method of fabrication is laser cutting. Other methods such as chemical etching or micro-machining may also be used. Nano-fabrication may also be an acceptable way of forming small microbarbs. Other microbarbs have been fabricated by building out layers of silicon to form microbarbs in the range of 100 microns high by 80 microns wide, which structures resemble slanted pyramids. The microbarbs 20 may be cut from a surface of the cylindrical body 12, as shown in FIG. 10. In this case, the microbarbs 20E are arranged with a plurality of microbarbs being aligned in successive rows. This configuration is exemplary only, and those skilled in the art will appreciate that other arrangements, including a random arrangement of unidirectional microbarbs, or a multidirectional, are possible.

The microbarbs 20 will have the same material when being formed by laser cutting the configuration into the cylindrical body. As discussed previously, the material can be stainless steel or nitinol among others. On the other hand, when incorporating microbarbs to the cylindrical body, it is desirable that material of the microbarbs be the same as the material of the cylindrical body. The microbarbs can be cut into a ring of material, which is then attached to the cylindrical body through known means of welding, soldering or the like. Other embodiments, however, may have different materials for the microbarbs and the cylindrical body. For example, FIGS. 11 and 12 illustrate the use of a microbarb formed from a shape memory composition, such as nitinol. In FIG. 11, the microbarb 20F is shown in a cold, or "open," position. Upon insertion into the vessel, the microbarb 20F transitions to a "closed" position when the microbarb 20F' reaches body temperature, as shown in FIG. 12. In such instances, the microbarbs 20F can be formed of the shape memory composition and attached to the cylindrical body 12 of a different material, such as stainless steel. Transition of shape memory compositions in the body from a first configuration to a second configuration is well known in the art, and a skilled artisan can readily optimize the conditions required to effect the transition described and shown herein.

In a preferred embodiment of the vascular conduit, the vascular conduit 10 may also be used as a connector (shown as connectors 100A, 100B) disposed at a proximal end 117 and a distal end 118 of a generally cylindrical body 112 to form another embodiment of the vascular conduit 110, as shown in FIG. 13. The vascular conduit 110 has a size and shape suitable for placement within a body vessel, such as a blood vessel (either an artery or vein), and most particularly, for placement at the site of a vascular trauma. In particular, the vascular conduit 110 is especially suitable for procedures requiring lengthier conduits and/or environments requiring conduits with more flexibility. Referring to FIGS. 2 and 16, the first row of the anchoring means 14A may be adapted to engage the tissue within the body vessel in a manner the same or similar to the anchoring means 14 described herein. The second row of the anchoring means 14B may be adapted to engage the inner wall of the vascular conduit 110. The engagement of the anchoring means 14B can cause the engaging region 111 to protrude radially outward. The general outer surface of the cylindrical body 12 of the connector 100 should be sized and configured to engage sealably the luminal wall of the cylindrical body 112 of the vascular conduit 110 and/or the luminal wall of the body vessel.

In FIG. 13, the generally cylindrical body 112 comprises a hollow, elongated, generally flexible material, such as a flexible polymeric material, having a lumen 116 extending therethrough. The lumen 116 of the cylindrical body 112 can be in communication with the lumen of the connectors 100A, 100B. The cylindrical body 112 can be formed from conventional materials well-known in the medical arts. A particularly preferred material is expanded polytetrafluoroethylene (ePTFE). Other materials that may be suitable in a particular case include, among others, silicone, polyurethane, polyamide (nylon), as well as other flexible biocompatible materials. If desired, the cylindrical body 112 can comprise a multi-layered structure of a type know in the art, and may also include a reinforcing member, such as a helical coil or braid, to inhibit kinking of the cylindrical body 112.

The cylindrical body 112 can also be formed from known fabric graft materials such as woven polyester (e.g. DACRON®), or from a bioremodelable material. A bioremodelable material can provide an extracellular matrix that permits, and may even promote, cellular invasion and ingrowth into the material upon implantation. Non-limiting examples of suitable bioremodelable materials include reconstituted or naturally-derived collagenous materials. Suitable collagenous materials may include an extracellular matrix material (ECM) that possesses biotropic properties, such as submucosa, renal capsule membrane, dermal collagen, dura mater, pericardium, fascia lata, serosa, peritoneum or basement membrane layers. Suitable submucosa materials may include, for example, intestinal submucosa, including small intestinal submucosa, stomach submucosa, urinary bladder submucosa, and uterine submucosa. A one-step process may be used to create the cylindrical body 112, as opposed to the multi-step process used in conventional ePTFE structures that often require reinforcement structures, such as spiral reinforcement, that are sutured or otherwise attached to the cylindrical body. The one-step process preferably results in one layer of ePTFE having a higher kink-resistance than with conventional ePTFE structures, without having the reinforcement structures. Higher kink resistance is desirable because of the dynamic movement of the body vessels and the body and to resist compressive forces due to the surrounding muscle tissue, organs, and the like.

An alternative connector 120 is shown in FIG. 14. The connector 120 may comprise any shape suitable for affixation with the proximal end 117 or distal end 118 portion of cylindrical body 112. The connector 120 can include an elongated tubular structure 123 having a larger diameter body portion 125, and two smaller diameter extended portions 126, 128 extending in opposite directions therefrom. The larger diameter body portion 125 provides a flange for both the vascular conduit and body vessel to help seal and prevent blood from leaking. The smaller diameter portion 126 is structured for affixation to the proximal end 117 or the distal end 118 of the cylindrical body 112, as shown in FIG. 15. In the embodiment shown, the smaller diameter portion 126 is received in the lumen 116 of the cylindrical body 112. The smaller diameter portion 126 is sized to fit snugly, such as via a friction fit, within the lumen 116 of the cylindrical body 112, or using a compressive ring. The smaller diameter portion 126 may be adapted to engage the inner wall of the vascular conduit 110' in place of the second row of the anchoring means 14B in FIGS. 2 and 13.

Referring to FIG. 14, structures may be provided on the smaller diameter portion 126, such as the annular recessed portions 127 shown thereon, to further enhance the connection with the lumen 116 of the cylindrical body 112. As another alternative, instead of the recessed portions 127, raised rings, nubs, or the like may be provided along all or part of the circumference of the smaller diameter portion 126 to enhance the connection. Preferably, the outer diameter of larger diameter body portion 125 will closely approximate the outer diameter of the cylindrical body 112 following affixation of the connectors 120A, 120B, as shown in FIG. 15. The larger diameter body portion 125 may have an annular recess in at least the side facing the cylindrical body 112 in order for the end of the cylindrical body 112 to fit snugly within the annular recess. The annular recesses may also include barbs or nubs to further secure the end of the cylindrical body 112 into annular recesses. Optionally, the larger diameter body portion 125 may have a portion with a reduced diameter to function as a flange that is configured to receive the end of the cylindrical body 112. The flange being sized to fit snugly within the lumen of the cylindrical body 112. The outer surface of the flange may have barbs or nubs to further secure the end of the cylindrical body 112 into the flange.

The smaller diameter portion 128 extends in the opposite axial direction from the larger diameter portion 125 when compared to the smaller diameter portion 126. The smaller diameter portion 128 is equipped with an anchoring means 114, which is described herein in relation to the anchoring means 14, distributed along all or part of the circumference of smaller diameter portion 128, as shown in FIG. 14.

Generally, similar to the cylindrical body 12 of the vascular conduit 10, the connector 120 comprises biocompatible material having a relatively rigid structure, such as a metal, metal alloy, or a high-strength polymer, having a lumen 130 therethrough along the longitudinal axis 119. Generally, any biocompatible composition having the requisite strength may be utilized, as long as the composition has sufficient strength to maintain its relative dimension in use. Although FIG. 14 illustrates one preferred shape of the connector 120 for use in vascular conduit 110', the connector 120 need not necessarily have the shape shown therein. For example, if desired, the axial end of the smaller diameter portions 126, 128 may include a taper 132 for ease of entry into the vessel undergoing repair.

The vascular conduit for use in open surgical, or intraoperative, placement according to the present invention need not necessarily be configured as shown and described herein. Other configurations are also suitable for such placement and are considered within the scope of the invention. For example, the cylindrical body of the vascular conduit may be formed to be selectively expandable from a collapsed, or "non-expanded," condition, to an expanded condition. In such case, the cylindrical body may comprise an elongated, generally cylindrical stent, which stent may be formed, e.g., of one or more wires in a conventional stent crossing pattern of wires. A fabric graft may be provided to cover the stent body in well-known fashion. The wires forming the stent body may be any conventional wires commonly utilized for such purposes, such as metals and metal alloys. Non-limiting examples of suitable compositions include stainless steel and shape memory materials, such as nitinol, as well as compositions that are visible under common medical imaging techniques such as magnetic resonance imaging (MRI). The fabric graft may comprise any graft material well-known in the medical arts, including, but not limited to, the materials described above with reference to the vascular conduit. In this case, the graft material must be capable of expansion. EPTFE is a particularly preferred graft material. Further description of such structures is provided in the incorporated-by-reference patent publication U.S. Patent Publication No. 2007/0027526 A1. Those skilled in the art will appreciate that other known types of stents and graft materials may be substituted for those shown and described herein.

According to the present invention, the vascular conduit is configured having materials and attachment means to permanently be placed within the patient, thereby obviating a need for subsequent surgical intervention. The overall length of the vascular conduit 110 can have virtually any dimensions for use in treating a vascular trauma. The application of the vascular conduit will dictate the length suitable to treat the condition. It is preferred that the vascular conduit will be slightly longer than the length of the damaged vascular portion undergoing repair. For convenience, the vascular conduit can be structured such that at least a portion of either, or both, axial ends of the cylindrical body can be trimmed by the physician to a desired length before engaging both connectors.

The vascular conduit described herein can also include a coating of one or more therapeutic agents. Therapeutic agents for use as bio-compatible coatings are well known in the art. Non-limiting examples of suitable bio-active agents that may be applied to the stent/graft device include thrombo-resistant agents, antibiotic agents, anti-tumor agents, antiviral agents, anti-angiogenic agents, angiogenic agents, anti-mitotic agents, anti-inflammatory agents, angiostatin agents, endostatin agents, cell cycle regulating agents, genetic agents, including hormones such as estrogen, their homologs, derivatives, fragments, pharmaceutical salts and combinations thereof. Those skilled in the art will appreciate that other bio-active agents may be applied for a particular use. The bio-active agent can be incorporated into, or otherwise applied to, portions of the stent/graft device by any suitable method that permits adequate retention of the agent material and the effectiveness thereof for its intended purpose.

Although the device has been described in connection with its primary intended use for repair of vascular trauma, those skilled in the art will appreciate that the device may also be used to repair other traumatic conditions. Non-limiting examples of such conditions include aneurysms, such as abdominal aorta aneurysms, and surgery for tumor removal.

FIG. 16 illustrates the connector 100 of the vascular conduit 110 engaging with the body vessel 200 and the flexible body 112. It can be appreciated that the connector 100 illustrated here can be instead a vascular conduit 10 as described herein engaging and bridging two portions of the body vessel. The connector 100 includes the first and second anchoring means 14A, 14B comprising a plurality of microbarbs. The microbarbs of the first anchoring means 14A are shown to penetrate preferably the tunica intima 206 and into the tunica media 204, avoiding penetration of the tunica adventitia 202.

The microbarbs of the second anchoring means 14B are shown to penetrate the wall of the cylindrical body 112. As shown, the tubular body 12 of the connector 100 can sealably engage with the luminal walls of the respective cylindrical body 112 and the body vessel 200 to prevent any leakage of blood and to force blood to flow within the lumens of the respective flexible body, connectors, and body vessel.

In a second embodiment, a delivery system 210 is provided to deliver and to deploy the vascular conduit as described herein, as well as other tubular medical devices. The delivery system 210 may have any suitable configuration to contain the vascular conduit 10 while protecting body tissue from the anchoring means 14, such as the microbarbs 20, at either the proximal and/or distal end 17, 18 of the vascular conduit 10. For example, FIGS. 17C and 18A illustrate the delivery system 210 including a dilator tip 214 with a proximal end 216 that at least partially encloses the anchoring means 14, such as the microbarbs 20, around the distal end 18 of the vascular conduit 10 surrounding an elongated tubular member 212. The dilator tip 214 can be configured to engage with the anchoring means 14.

Referring specifically to FIG. 19, the dilator tip 214 preferably has a conical shape with a distal end 218. The dilator tip 214 is tapered at an angle β, where the angle β can range between about 15 degrees to about 45 degrees, although any angle may be suitable to ensure penetration in to the lumen of the body vessel and protection of the anchoring means 14 during delivery. The angle β should be suitable to ensure that the proximal end 216 of the dilator tip can partially enclose the anchoring means 14 of the vascular conduit 10. The distal end 218 preferably is blunt to ensure that the dilator tip 214 does not penetrate through the body vessel wall when being inserted. The outer diameter of the blunt distal end 218 can range between 50% to about 85% of the outer diameter of the proximal end 216. The dilator tip 214 may have a cavity 220 with an opening through the proximal end 216. A wall of the dilator tip 214 is defined between the cavity 220 and the space exterior of the dilator tip 214. In one example, the dilator tip 214 has a tapering angle β of about 20 degrees, an outer diameter at the proximal end 216 of about 5 mm, an outer diameter at a blunt distal end 218 of about 2 mm, and a general length of about 12 mm. The dilator tip wall thickness can be 0.5 mm to about 1 mm. The dilator tip 214 can comprise various elastic biocompatible materials, such as silicone, polyurethane, or the like and can be preferably molded depending by the material, for example, the dilator tip molded by compression molding or injection molding.

The proximal end 216 of the dilator tip 214 can have a first cross-sectional area that is slightly less than the cross-sectional area of the lumen 16 of the cylindrical body 12 of the vascular conduit 10. Consequently, when the dilator tip 214 is in the extended position (FIG. 17B), the dilator tip 214 can be removed through the lumen 16 after deployment of the vascular conduit 10. The proximal end 216 preferably is adapted to expand radially to a second cross sectional area, in the retracted position (FIG. 17C) that is greater than the first cross-sectional area in order to engage with the anchoring means 14. When the dilator tip 214 is made of an elastic material, the dilator tip 214 can apply a radially compressive force to the anchoring means 14 to affix the vascular conduit 10 in place until deployment.

FIG. 17A illustrates one embodiment of the vascular conduit delivery system 210. The delivery system 210 can include the elongated tubular member 212, the dilator tip 214, a proximal handle 222, and a controller 224 for manipulating the dilator tip 214.

Referring to FIGS. 18A and 18B, the elongated tubular member 212 is used to support a tubular medical device, such as the vascular conduit 10, during delivery. The elongated tubular member 212 can be configured to have a flexibility to penetrate the body vessel wall at an angle substantially perpendicular with respect to the body vessel and to be aligned along the lumen of the body vessel after penetration. The elongated tubular member 212 may also be configured to have a suitable flexibility to curve easily during use such that the physician can maintain the proximal handle 222 substantially perpendicular to the body vessel and the deployed vascular conduit. Though the discussion is related to the delivery of the vascular conduit 10 primarily, it can be appreciated by one skilled in the art that the delivery system 212 can support other tubular medical devices, such as stents, grafts, valves or the like. The elongated tubular member 212 has a proximal end 230 and a distal end 232 and a support region 234 for supporting a tubular medical device, such as the vascular conduit. The vascular conduit 10 may be retained to the elongated tubular member 212 at the support region 234 by frictional engagement. For example, the support region 234 (FIG. 17B) of the elongated tubular member 212 can have a cross-sectional area slightly less than the cross-sectional area of the lumen 16 of the vascular conduit 10 to permit a snug fit. Preferably, the vascular conduit 10 is capable of moving at the support region 234 and is engaged with the dilator tip 214 when retracted. Optionally, the thumb or finger of the physician may also further retain the vascular conduit 10 during deployment.

FIGS. 17B and 18B illustrate the elongated tubular member 212 having a tapered tip 236 at the distal end 232 of the elongated tubular member 212. The tapered tip 236 can be tapered at an angle similar to the angle B to guide the interior wall of the dilator tip 214 to the vascular conduit 10. The tapered tip 236 may also be tapered at an angle to promote flaring of the proximal end 216 of the dilator tip 214 to the second cross-sectional area in order to engage with and enclose the vascular conduit 10 partially. The distal end 232 and the tapered tip 236 of the elongated tubular member 212 can be sized and shaped to extend through the proximal end 216 and into the cavity 220 of the dilator tip 214. A lumen 238 can also be defined between the proximal and distal ends 230, 232 of the elongated support member 212.

The proximal handle 222 is ergonomically sized and shaped to fit within the hand of the physician. FIGS. 18A and 18B illustrate the proximal handle 222 having a proximal end 240 and a distal end 242 and a lumen 244 extending therebetween. The lumen 244 of the proximal handle 222 has cross-sectional area slightly larger than the cross-sectional area of the outer surface of the elongated tubular member 212 to receive a portion of the elongated tubular member 212. The lumen 244 of the proximal handle 222 and the lumen 238 of the elongated tubular member 212 can be in fluid communication. The elongated tubular member 212 may be affixed or bonded to the proximal handle 222 by a means known by one skilled in the art.

The proximal handle 222 can also provide a housing for the controller 224. The controller 224 provides a means for manipulating the dilator tip 214 in order to protect the vessel from the tubular medical device during deployment and to remove the delivery system after deployment. Preferably, the controller 224 permits the dilator tip 214 to translate axially between a retracted position (FIG. 18A) and an extended position (FIG. 18B). At the retracted position, the dilator tip 214 can partially enclose the anchoring means 14B of the vascular conduit 10, as shown in FIG. 17C. Transitioning between the retracted and extended position can permit the anchoring means 14A, 14B of the vascular conduit 10 to anchor within the walls of the body vessel 200 and/or flexible body 112, as described herein. At the extended position, the dilator tip 214 is permitted to be withdrawn through the lumen 16 of the engaged vascular conduit 10, and the delivery system 210 can be completely withdrawn from the body vessel 200.

The controller 224 can include a control member 248 that is configured to axially extend from a proximal end 250 to a distal end 252 through the lumens 244, 238 of the respective proximal handle 222 and the elongated tubular member 212, and terminating at the dilator tip 214. The control member 248 can be configured to have a suitable stiffness to translate pushability forces from the switch 260 and a flexibility similar to the elongated tubular member 212. The control member 248 can include a wire, a strand of wires, a rod, or a cannula made of a biocompatible metal or polymer. In FIG. 19, the control member 248 is a strand of wires with a binding means 254 at each end of the strand of wires. The control member 248 can also include wall-engaging members 256, such as microbarbs, to penetrate the wall of dilator tip 214. A filler 258, such as an epoxy or silicone adhesive, can be included into the cavity of the dilator tip 214 to further secure the attachment of the control member 248 to the dilator tip 214. The proximal end 250 of the control member 248 is further seated or attached to a portion of the controller 224. For example, the proximal end 250 may include a binding means and/or microbarb-like structures, and may be molded into, or otherwise formed, into a switch 260 or button, as shown in FIGS. 18A and 18B.

The switch 260 is movable between a first position (FIG. 18A) and a second position (FIG. 18B). The switch 260 can be maintained at the first position by a spring mechanism 262 having one end abutting a bushing ring 263 that is engaged with the proximal handle 222 and the other end abutting the movable switch 260. The spring mechanism 262 is axially movable between an expanded configuration, when the switch 260 is at the first position, and a compressed configuration, when the switch 260 is at the second position. The spring mechanism 262 can include a spring, an elastic member or the like. The switch 260 preferably has a flange 264 configured to engage a shoulder 266 within the lumen 244 of the proximal handle 222 to prevent the switch 260 from being displaced out of the lumen 244 of the proximal handle 222 and to maintain the switch 260 at the first position. The switch 260 can be sized and configured to slide within the lumen 244 of the proximal handle 222 by urging the switch 260 to the second position, which urges the spring mechanism 262 to retract to the compressed configuration.

The switch 260 also preferably has a locking means 268 configured to maintain the switch 260 at the second position. For example, the locking means 268 can include a spring loaded member being movable between a compressed configuration, when the switch 260 is at the first position, and an expanded configuration, when the switch 260 is at the second position. A port 270 can be included into the wall of the proximal handle 222 to allow the spring loaded member to expand through the port 270. The spring loaded member can be sized and configured to slide within the port 270 and to lock into place until the spring loaded member is urged to retract to the compressed configuration by the physician. It can be appreciated that the switch 260 can be locked or retained into a position in other means known by one skilled in the art.

FIGS. 20A-B illustrate the loading of one exemplary vascular conduit onto the delivery system. The vascular conduit 110 includes the flexible body 112 and one connector 100.

The vascular conduit 110 is loaded onto the delivery system 210 by inserting the dilator tip 214, in the extended position, through the lumens 16, 116 of the respective connector 100 and the flexible body 112. Once the dilator tip 214 and the distal end 232 of the elongated tubular member 212 is extended past the distal end 18 of the connector 100, the distal end 232 of the elongated tubular member can be disposed proximate the distal end 18 of the connector 100. The dilator tip 214 can be moved from the extended position to the retracted position. In the retracted position, the proximal region 217 of the dilator tip 214 applies radial compression to the connector 100 of the vascular conduit 110 to engage and prevent the vascular conduit 210 from translating during delivery until being deployed, as shown in FIG. 17C.

Other embodiments of the delivery system are shown in FIGS. 21A and 22, which are substantially similar to the delivery system 210 described above except for the following. In FIG. 21A, the delivery system 310 includes a rotatably mounted proximal handle 322 having a lumen. The proximal handle 322 includes a threaded portion 324 that receives a structure 326 capable of threadably engaging with the treaded portion 324. FIG. 21B illustrates the threaded portion 324, as internal threads, receiving the structure 326 that is disposed at the proximal end 314 of the elongated tubular member 312. The proximal handle 322 includes a cap 328 being configured to receive the proximal end 252 of the support member 248. The cap 328 is preferably molded to the proximal handle 322. The rigidity of the support member 248 can be maintained with the relative movement of the proximal handle 322 which causes the dilator tip 214 to move. Rotating the proximal handle 322 in a first direction, represented by arrow 330, causes the elongated tubular member 312 to move in the distal direction, relative to the dilator tip 214. Continuing to rotate the proximal handle 322 urges the dilator tip 214 to the retracted position. Rotating the proximal handle 322 in a second direction, opposite the first direction, represented by arrow 332, causes the elongated member 312 to move in the proximal direction relative to the dilator tip 214. Continuing to rotate the proximal handle in the second direction urges the dilator tip 214 to the extended position. A locking means and/or a spring mechanism (both not shown) may be provided to maintain the dilator tip 214 in the fully extended position and/or fully retracted position.

In FIG. 22, the delivery system 410 includes a proximal handle 422 having a slot 424 and a cross member 426 slidably mounted to the proximal handle 422 through the slot 424. The proximal handle 422 is attached to the elongated tubular member 412. The cross member 426 is movable between a first position (FIG. 22) and a second position (shown in dashed lines). The cross member 426 is configured to receive the proximal end of the support member 248. Sliding the cross member 426 to the first position causes the dilator tip 214 to move to the retracted position. Sliding the cross member 426 to the second position causes the dilator tip 214 to move to the extended position.

In another embodiment, elongating or stretching the dilator tip can radially compress the proximal region of the dilator tip from an expanded configuration to a compressed configuration. For example, the dilator tip and/or the control member may be made of a material and/or into a certain geometry that allows the dilator tip to be stretched along the axial direction. When in the expanded configuration (unstretched), the dilator tip applies a radially compressive force to the loaded vascular conduit. Stretching the dilator tip can permit the proximal region of the dilator tip to be removed from the vascular conduit and to be radially compressed to the first cross-sectional area that is less than the cross-sectional area of the lumen of the vascular conduit. The dilator tip may be removed through the lumen of the vascular conduit, as described herein.

In a third embodiment, methods of deploying a tubular medical device, such as one of the embodiments of the vascular conduit, within a body vessel via open surgical placement are provided. The following is provided to facilitate the understanding of the structure and use of the inventive vascular conduit 10. A body vessel that has previously been subjected to a traumatic episode may have a portion of the body vessel torn away or otherwise severely damaged. In one aspect, without transecting the body vessel, the vascular conduit 10 can be manually placed within body vessel by the physician, in a manner such that cylindrical body spans at least the length of damaged vessel portion intravascularly without transecting the body vessel. To prevent blood loss through the open portion of the body vessel, a vessel puncture means attached to a guiding means may be inserted into the open portion of the body vessel. The puncture means is preferably a curved needle suitable for passage through the wall of the body vessel and other tissue between the body vessel and the cutaneous surface of the patient. The guiding means is preferably a thread or wire guide suitable for guiding a vascular conduit delivery system through the body vessel. The vessel puncture means may be inserted into the body vessel through the open portion and translated to a puncture site within the body vessel, where the puncture means is passed through the wall of the body vessel. The puncture means and guiding means are passed through the puncture site and brought out of the body.

The distal end of the guiding means may be pulled into the body vessel and advanced to a site distal to the open portion of the body vessel. The delivery system, which may be similar to the delivery system described herein, is advanced from outside the body along the guiding means and inserted into the body vessel at the puncture site. This procedure may be performed using a series of steps, for example by using a dilator and additional intermediate catheters to dilate the puncture site prior to inserting the delivery system. For example, the insertion of the delivery system may be performed using the Seldinger technique, as known to one of skill in the art.

The delivery system is advanced through the body vessel along the guiding means until the vascular conduit is positioned across the open portion, where the vascular conduit is deployed, with the anchoring means of the vascular conduit penetrating and anchoring into the walls of the body vessel. Once the vascular conduit is placed within the blood vessel bridging the open portion, the delivery system is removed through the lumen of the cylindrical body and out of the body vessel at the puncture site along the guiding means. The guiding means is removed from the body vessel, out of the puncture site, which is then closed, for example using a vascular closure device. The open portion of the body vessel is now closed by the cylindrical body of the vascular conduit. Optionally, the vascular conduit can include a flexible tubular body with one attached connector. This vascular conduit can be inserted and implanted in the walls of the body vessel. The vascular conduit may be trimmed to size and a second connector may be implanted into the wall of the second vessel.

In a second aspect, the tubular medical device, such as a vascular conduit 510 which is exemplary of other embodiments, can be deployed using the following, as shown in FIGS. 23A-E. FIG. 23A illustrates a blood vessel 500 that has previously been subjected to a traumatic episode. In this case, it will be observed that a portion 502 of blood vessel 500 has been torn away or otherwise severely damaged. After clamping the blood vessel 500 on both ends of the portion 502 to restrict blood flow temporarily, the blood vessel 500 can be cut or transected into two portions 500A, 500B. The transecting may be at the removed portion 502 of the blood vessel 500 or just outside the removed portion 502. Sutures 504 can be attached to the ends of the body vessel portions 500A, 500B to keep the portions 500A, 500B fixed in place and to keep the vessel lumen opened for insertion of the vascular conduit 510, as shown in FIGS. 23B-E. Although four sutures are shown, preferably, triangulation sutures are attached, with each suture being about 120 degrees apart from the adjacent suture.

The vascular conduit 510 can be formed by cutting a piece of flexible tubular body 512 and flaring one end 514 of the flexible tubular body 512 with a dilator tool, such as dilating forceps. The flexible tubular body 512 is gently flared to receive the connector 520. After inserting the connector 520, the flexible tubular body 512 is smoothed out to seat the anchoring means (not shown) of the connector 520 into the walls of the flexible tubular body 512. The vascular conduit 510, partially assembled, is then loaded onto the delivery system 530. FIGS. 20A-B are illustrative of the partially assembled vascular conduit, and of the loading of the partially assembled vascular conduit onto the delivery system.

In FIG. 23B, the dilator tip 532, in the retracted position, of the delivery system 530, with the partially assembled vascular conduit 510, is inserted into the opening of the first portion 500A of the blood vessel 500. The delivery system 530, similar to the delivery systems described herein, is advanced into the lumen 506A of the first portion 500A of the blood vessel 500 until the connector 520 is positioned at a suitable distance from the axial end of the opening of the first portion 500A. The dilator tip 532 can be translated from the retracted position to the extended position in order to permit penetration and anchoring of the anchoring means 522 into the walls of the first portion 500A of the body vessel 500. The delivery system 530, with the dilator tip 532 in the extended position, can then be removed from the first portion 500A of the body vessel 500 through the lumens of the respective connector 520 and the flexible tubular body 512.

A connector 540 can then be loaded on the delivery system 530 in order for the connector 540 to be inserted into the second portion 500B of the body vessel 500, with FIG. 17C being illustrative of the loaded connector. Referring to FIG. 23C, the dilator tip 532, in the retracted position, of the delivery system 530 with the loaded connector 540, is inserted into the opening of the second portion 500B of the blood vessel 500. The delivery system 530 is advanced into the lumen 506B of the second portion 500B of the blood vessel 500 until the connector 540 is positioned at a suitable distance from the axial end of the opening of the second portion 500B. The dilator tip 532 can be moved from the retracted position to the extended position in order to permit penetration and anchoring of the anchoring means 542A into the walls of the second portion 500B of the body vessel 500. The delivery system 530 can then be removed from the second portion 500B of the body vessel 500. The sutures 504 can then be removed.

A portion of the flexible tubular body 512 can be cut or trimmed to a suitable length. The axial end 516 of the flexible tubular body 512 can be flared by the dilator tool in order to receive the connector 540. Referring to FIG. 23D, the anchoring means 542B of the connector 540 may be inserted and engaged with the walls of the flexible tubular body 512 through the opening of the axial end 516 to form the fully assembled vascular conduit 510' between the first and second portions 500A, 500B of the body vessel 500 and to repair the damaged portion of the body vessel 500 intraoperatively. The flexible tubular body 512 can be gently smoothed out to seat the anchoring means 542B into the walls of the flexible tubular body 512. FIG. 23E illustrates the fully assembled vascular conduit 510' engaging and bridging the first and second portions 500A, 500B of the body vessel 500 to form a passageway for blood flow. The body vessel portions 500A, 500B may be pulled away from each other in order to better seat the anchoring means 522, 542A within the walls of the body vessel. Preferably, portions of the exterior surfaces of the vascular conduit 510' sealably engages with the luminal walls of the body vessel 500 to prevent any leakage of blood and to force blood to flow throughout the body vessel 500 during emergency surgery, and particularly to obtain hemostasis while maintaining blood perfusion. Optionally, the connectors 520, 540 can deployed first at the respective first and second portions 500A, 500B of the body vessel, and the flexible tubular body 512 can be attached to the deployed connectors 520, 540 in the manner described herein. According to the present invention, the vascular conduit 510' can be permanently placed within the patient, thereby obviating a need for subsequent surgical intervention.

It is therefore intended that the foregoing detailed description be regarded as illustrative rather than limiting, and that it be understood that it is the following claims, including all equivalents, that are intended to define the spirit and scope of this invention.

We claim:

1. A method for open surgical repair of a damaged portion of a body vessel having a vessel wall defining a lumen, the vessel wall including a tunica intima, a tunica media, and a tunica adventitia, the steps comprising:
    providing a medical device including a first connector and a second connector and a tubular conduit, the tubular conduit having a wall defining a lumen about a longitudinal axis between a first axial end and a second axial end, and the first and second connectors disposable with the respective first and second axial ends of the tubular conduit, each of the first and second connectors having a first portion engageable with the wall of the tubular conduit, and a second portion having a plurality of shaped members dimensioned and arranged therealong to penetrate and anchor into the vessel wall;
    transecting said body vessel to form a first portion and a second portion of said body vessel;
    deploying the first and second connectors of the medical device into the respective first and second portions of said body vessel with a delivery system, such that the shaped members of the first and second connectors penetrate and anchor into the tunica intima and tunica media of the respective first and second body vessel portions, and not into the tunica adventitia; and
    engaging the first axial end of the tubular conduit to the first connector and the second axial end of the conduit to the second connector to form the medical device to repair the damaged portion of the body vessel.

2. The method of claim 1, wherein the delivery system comprises a dilator tip sized and configured to engage the at least one shaped member of the second portion of the respective first and second connectors, wherein the dilator tip is movable between a retracted position to engage with the at least one shaped member and an extended position to disengage from the at least one shaped member.

3. The method of claim 1, wherein the tubular conduit is engaged with the first connector, and the first connector including the tubular conduit is deployed into the first portion of said body vessel with the delivery system.

4. A method for open surgical repair of a damaged portion of a body vessel of a patient, the body vessel having a vessel wall including a tunica intima, a tunica media, and a tunica adventitia, comprising:
  loading a medical assembly onto a delivery system for deployment at said damaged vessel portion, the medical assembly comprising a tubular conduit having a first axial end and a second axial end, and a first connector disposed at said first axial end, said first connector comprising a first portion engaged with the first axial end of the tubular conduit and a second portion having a plurality of microbarbs dimensioned and circumferentially arranged along a surface thereof to penetrate and to anchor into the wall of said body vessel;
  transecting said damaged body vessel through an open surgical pathway to form a first end portion and a second end portion of said body vessel;
  advancing an end of the delivery system through the open surgical pathway into said first end portion of the body vessel such that said microbarbs penetrate and anchor into the tunica intima and tunica media of the body vessel wall, and not into the tunica adventitia;
  removing said delivery system end from the first vessel end portion;
  loading a second connector onto said delivery system, said second connector comprising a first portion engageable with the second axial end of the tubular conduit and a second portion having at least one shaped member dimensioned and arranged along a surface thereof to penetrate and to anchor into the wall of said body vessel;
  advancing an end of the delivery system through the open surgical pathway into said second end portion of the body vessel such that the at least one shaped member of the second connector penetrates and anchors into the body vessel wall; and
  joining the first portion of the second connector with the second axial end of the tubular conduit.

5. The method of claim 4, wherein the delivery system comprises a dilator tip sized and configured to engage the microbarbs of the first connector, the dilator tip axially movable between a retracted position for engagement with the microbarbs upon advancement of the delivery system into the first end portion of the body vessel, and an extended position for disengagement from the first connector upon removal of the delivery system from the first vessel end portion.

6. The method of claim 5, wherein the dilator tip has a conical shape tapering from a proximal end to a blunt distal end.

7. The method of claim 5, wherein the dilator tip is sized and configured to engage the at least one shaped member of the second connector, the dilator tip being movable between a retracted position for engagement with the at least one shaped member of the second connector upon advancement of the delivery system into the second end portion of the body vessel, and an extended position for disengagement from the second connector upon a removal of the delivery system from the second vessel end portion.

8. The method of claim 4, further comprising the step of trimming a length of the second axial end of the tubular conduit after said advancing steps are carried out and prior to joinder with the second connector.

9. The method of claim 4, wherein the microbarbs are spaced along said circumference of the tubular body to form at least one ring of microbarbs, and wherein the tubular conduit comprises a flexible biocompatible material selected from the group consisting of expanded polytetrafluoroethylene, silicone, polyurethane, and polyamide.

10. The method of claim 4, further comprising the step of suturing the first end portion following transection of said damaged vessel for facilitating advancement of said delivery system end.

11. The method of claim 4, wherein the microbarbs are arranged in a plurality of rings of microbarbs spaced along a circumference of said surface.

12. A method for open surgical repair of a damaged portion of a body vessel of a patient, the body vessel having a vessel wall including a tunica intima, a tunica media, and a tunica adventitia, comprising:
  transecting the body vessel at said damaged portion through an open air surgical pathway to form a first vessel end portion and a second vessel end portion;
  positioning a first connector for insertion through said open air pathway, said first connector comprising a first portion and a second portion, said second portion having at least one shaped member dimensioned and arranged along a surface thereof to penetrate and anchor into a wall of the first vessel end portion, said at least one shaped member of said first connector comprising a plurality of microbarbs spaced along a circumference of said surface, and inserting said second portion of said first connector through said open air pathway into said first vessel end portion a distance such that said microbarbs penetrate and anchor into the tunica intima and tunica media of said wall of said first vessel end portion, and not into the tunica adventitia;
  positioning a second connector for insertion through said open air pathway, said second connector comprising a first portion and a second portion, said second portion having at least one shaped member dimensioned and arranged along a surface thereof to penetrate and anchor into a wall of the second vessel end portion, and inserting said second portion of said second connector through said open air pathway into said second vessel wall portion a distance such that said at least one shaped member penetrates and anchors into said wall;
  inserting a first axial end of a tubular conduit through said open air pathway and thereafter joining said first axial end with the first portion of the first connector; and
  joining a second axial end of the tubular conduit with the first portion of the second connector.

13. The method of claim 12, comprising the step of trimming a length of at least one axial end of the tubular conduit after said advancing steps are carried out.

14. The method of claim 12, further comprising loading said first connector onto a delivery system for insertion into said first vessel end portion, and advancing an end of the delivery system through the open air pathway into the first vessel end portion.

15. The method of claim 14, wherein the delivery system comprises a dilator tip sized and configured to engage the at least one shaped member of the first connector, the dilator tip axially movable between a retracted position for engagement with the at least one shaped member upon advancement of the delivery system into the first end portion of the body vessel, and an extended position for disengagement from the first connector upon a removal of the delivery system from the first vessel end portion.

16. The method of claim 12, further comprising loading the second connector onto the delivery system for insertion into the second vessel end portion, and advancing an end of the delivery system through the open air pathway into the second vessel end portion.

* * * * *